(12) United States Patent
Cole et al.

(10) Patent No.: US 9,782,538 B2
(45) Date of Patent: Oct. 10, 2017

(54) ANGLED INSERTER FOR DRUG INFUSION

(71) Applicant: Becton, Dickinson and Company, Franklin Lakes, NJ (US)

(72) Inventors: Russell Cole, New York, NY (US); Arthur Klotz, Willow Grove, PA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 565 days.

(21) Appl. No.: 13/629,479

(22) Filed: Sep. 27, 2012

(65) Prior Publication Data

US 2014/0088549 A1 Mar. 27, 2014

(51) Int. Cl.
*A61M 5/158* (2006.01)
*A61M 5/142* (2006.01)
*A61M 5/46* (2006.01)

(52) U.S. Cl.
CPC ........ *A61M 5/158* (2013.01); *A61M 5/14248* (2013.01); *A61M 5/46* (2013.01); *A61M 2005/14252* (2013.01); *A61M 2005/1585* (2013.01); *A61M 2005/1587* (2013.01)

(58) Field of Classification Search
CPC .... A61M 5/14248; A61M 5/158; A61M 5/46; A61M 2005/14252; A61M 25/065; A61M 2005/1581; A61M 2005/1585
See application file for complete search history.

(56) References Cited

U.S. PATENT DOCUMENTS

| | | | |
|---|---|---|---|
| 5,522,803 A | 6/1996 | Teissen-Simony |
| 5,688,254 A | 11/1997 | Lopez |
| 5,776,116 A | 7/1998 | Lopez |
| 5,980,506 A | 11/1999 | Mathiasen |
| 6,017,328 A | 1/2000 | Fischell |
| 6,086,575 A | 7/2000 | Mejslov |
| 6,123,690 A | 9/2000 | Mejslov |
| 6,293,925 B1 | 9/2001 | Safabash |
| 6,607,509 B2 | 8/2003 | Bobroff |
| 7,052,483 B2 | 5/2006 | Wojcik |
| 7,303,543 B1 | 12/2007 | Maule |
| 7,329,239 B2 | 2/2008 | Safabash |
| 7,364,568 B2 | 4/2008 | Angel et al. |
| 7,713,258 B2 | 5/2010 | Adams |
| 8,172,803 B2 | 5/2012 | Morrissey |

(Continued)

FOREIGN PATENT DOCUMENTS

EP 1170024 9/2002
EP 2327433 A1 6/2011
(Continued)

*Primary Examiner* — Nathan R Price
*Assistant Examiner* — Justin L Zamory
(74) *Attorney, Agent, or Firm* — Dickinson Wright PLLC

(57) ABSTRACT

An infusion set adapted to be secured to a skin surface includes a fixed base member and a movable slide member. The fixed base member is connectable to the skin surface. The movable slide member has a needle or cannula connected thereto and is movable relative to the fixed base member. The movable slide member is movable from a first position in which the needle or cannula is not exposed externally of the fixed base member to a second position in which the needle or cannula is exposed externally of the fixed base member. The movable slide member is locked to the fixed base member in the second position.

19 Claims, 29 Drawing Sheets

(56) References Cited

U.S. PATENT DOCUMENTS

| | | |
|---|---|---|
| 8,246,582 B2 | 8/2012 | Angel et al. |
| 2002/0077599 A1* | 6/2002 | Wojcik ................. A61M 5/158 604/162 |
| 2006/0184104 A1 | 8/2006 | Cheney, II |
| 2006/0247574 A1 | 11/2006 | Maule et al. |
| 2007/0282269 A1 | 12/2007 | Carter et al. |
| 2008/0045891 A1 | 2/2008 | Maule |
| 2008/0167620 A1 | 7/2008 | Adams |
| 2008/0208139 A1 | 8/2008 | Scheurer et al. |
| 2009/0012472 A1 | 1/2009 | Ahm et al. |
| 2009/0131860 A1* | 5/2009 | Nielsen ............. A61M 5/14248 604/66 |
| 2009/0192471 A1 | 7/2009 | Carter et al. |
| 2009/0254041 A1 | 10/2009 | Krag |
| 2011/0040256 A1 | 2/2011 | Bobroff |
| 2012/0136299 A1* | 5/2012 | Constantineau ...... A61M 5/158 604/117 |

FOREIGN PATENT DOCUMENTS

| | | |
|---|---|---|
| EP | 2457604 A1 | 5/2012 |
| JP | 9-507779 | 8/1997 |
| JP | 2010-501211 A | 1/2010 |
| WO | 2006108809 A1 | 10/2006 |
| WO | 2008022476 A1 | 2/2008 |
| WO | 2009016638 A1 | 2/2009 |

\* cited by examiner

ANGLED INSERTER FOR DRUG INFUSION

FIELD OF THE INVENTION

The present invention relates generally to angled infusion sets, particularly angled intradermal infusion sets. More particularly, the present invention relates to angled intradermal infusion sets having a removable inserter that prevents partial needle insertion. More particularly, the present invention relates to angled intradermal infusion sets in which a direction of user motion is different from a direction of needle insertion.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which a hollow infusion needle or cannula extends. The hub or base has an adhesive which retains the base on the skin surface during use, which may be applied to the skin manually or with the aid of a manual or automatic insertion device.

Currently, most insulin infusion sets deliver insulin to the subcutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

One technique to provide intradermal injection is the Mantoux technique. As known to those skilled in the art, the Mantoux technique is typically used when administering tuberculosis tests. Skilled practitioners first stretch taut the selected area of skin between the thumb and forefinger, and then insert the needle slowly, bevel upward, at an angle of 5 to 15 degrees to the skin surface. The practitioner then advances the needle through the epidermis approximately 3 mm, releases the stretched skin, and injects the medicament. However, even where intradermal delivery can be accomplished with the standard Mantoux technique, this method is highly variable and subject to user error.

Most insulin infusion sets typically do not provide any features to isolate the inserted needle from shock or other external forces. Since those infusion sets typically deliver insulin 4-10 mm below the skin surface, shock or other external forces to the set have less effect on the deeper inserted needle. However, where an attempt is made to target the upper 3 mm of skin surface, any shock or movement of the set can adversely affect needle insertion and infusion performance.

Still further, most insulin sets have inserters that can result in skin surface "tenting" during needle insertion, where the skin surface is deflected somewhat prior to or during needle insertion which makes precisely targeting the upper 3 mm of skin surface difficult.

Accordingly, a need exists for an infusion set that can deliver content to the upper 3 mm of skin surface, the intradermal space, to facilitate better drug absorption, while maintaining a degree of comfort to the user.

SUMMARY OF THE INVENTION

An object of the present invention is to provide an infusion set that can insert a needle or cannula at an angle relative to a skin surface via a user motion, the angle of user motion being different from the angle of the inserted needle or cannula, to target and deliver insulin or other medicament to the upper 3 mm of skin surface.

Another object of the present invention is to provide an infusion set that can insert a needle or cannula at an angle to duplicate the Mantoux insertion technique and deliver insulin or other medicament to the upper 3 mm of skin surface.

Another object of the present invention is to provide an infusion set having a skin-securing adhesive layer to secure the skin surface at the insertion site such that the set can insert a needle or cannula with a reduced risk of tenting of the skin surface and/or precisely target the intradermal depth.

In accordance with an exemplary embodiment of the present invention, an infusion set is adapted to be secured to a skin surface includes a fixed base member and a movable slide member. The fixed base member is connectable to the skin surface. The movable slide member has a needle or cannula connected thereto and is movable relative to the fixed base member. The movable slide member is movable from a first position in which the needle or cannula is not exposed externally of the fixed base member to a second position in which the needle or cannula is exposed externally of the fixed base member. The movable slide member is locked to the fixed base member in the second position.

In accordance with another exemplary embodiment of the present invention, an inserter for inserting a needle or cannula of an infusion set includes a fixed inserter member and a movable inserter member movably connected to the fixed inserter member and adapted to receive the infusion set. The movable inserter member is movable from a first position to a second position to expose the needle or cannula. The movable inserter member is locked to the fixed inserter member in the first position to prevent accidentally exposing the needle or cannula.

In accordance with an exemplary embodiment of the present invention, an infusion set assembly includes an infusion set assembly adapted to be secured to a skin surface and an inserter removably connected to the infusion set for moving the movable slide member from a first position to a second position. The infusion set includes a fixed base member connectable to the skin surface, and a movable slide member having a needle or cannula connected thereto and movable relative to the fixed base member. The movable slide member is movable from the first position in which the needle or cannula is not exposed externally of the fixed base member to a second position in which the needle or cannula is exposed externally of the fixed base member.

In accordance with an exemplary embodiment of the present invention, a method of intradermally inserting a needle or cannula of an infusion set includes placing an infusion set having a needle or cannula on an infusion site. An inserter connected to the infusion set is moved in a first direction to move a slide member of the infusion set from a first position to a second position in which the needle or cannula is inserted in the infusion site at a non-perpendicular angle and in which the needle is moved in a second direction different from the first direction.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The various objects, advantages and novel features of the exemplary embodiments of the present invention will be more readily appreciated from the following detailed description when read in conjunction with the appended drawing figures, in which.

Throughout the drawings, like reference numerals will be understood to refer to like parts, components and structures.

DETAILED DESCRIPTION OF THE EXEMPLARY EMBODIMENTS

Figure 1:
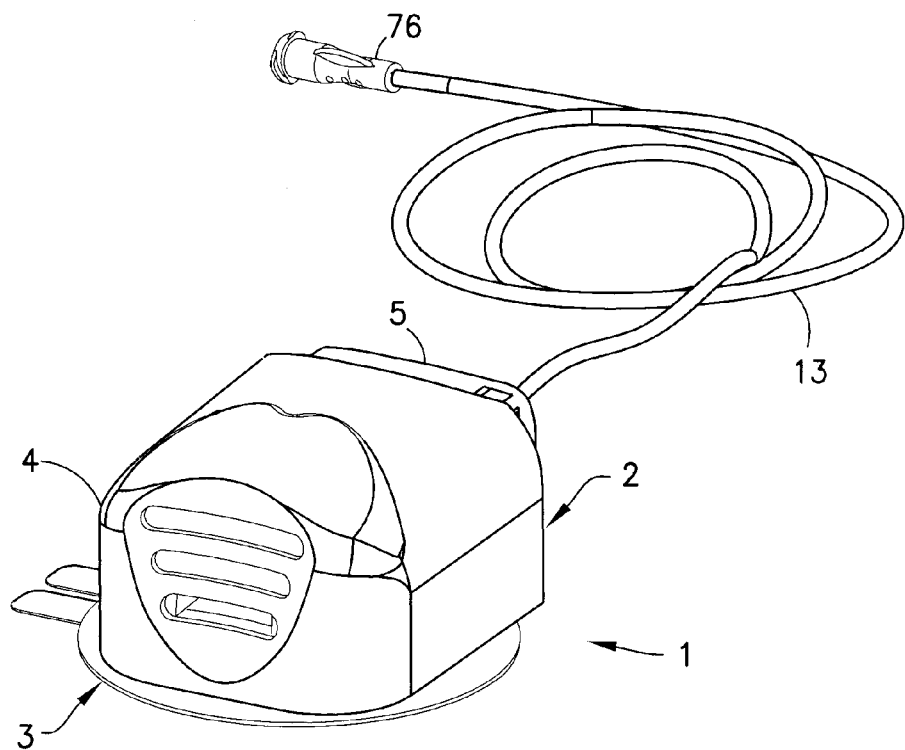
FIG. 1 is a perspective view of an infusion set and inserter in accordance with an exemplary embodiment of the present invention.
Figure 52:
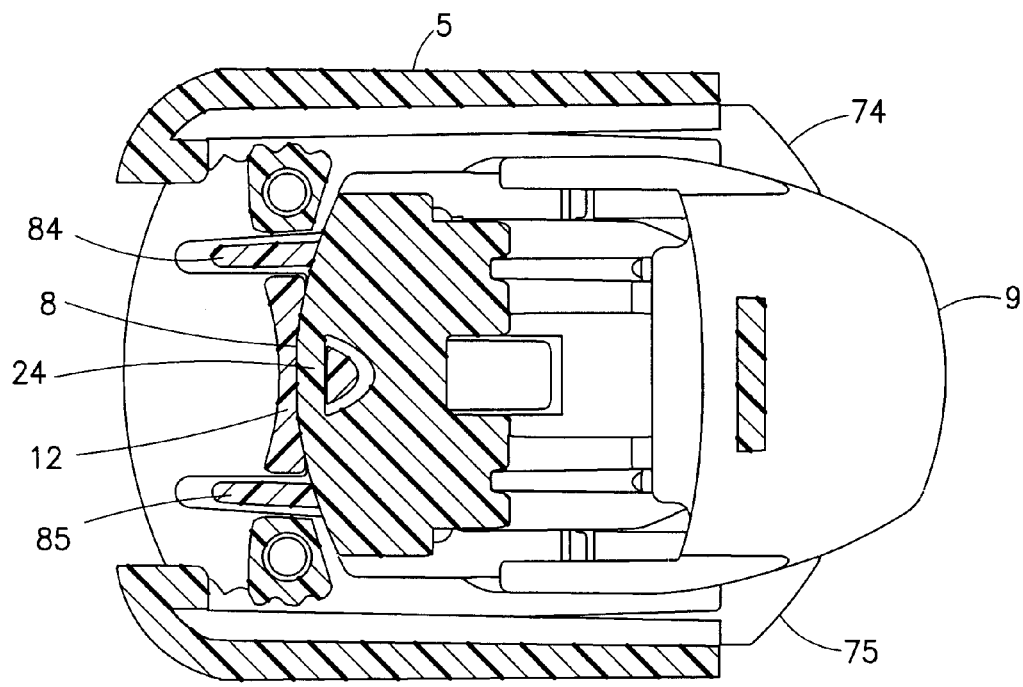
FIG. 52 is a top plan view in cross section of a connector tab of the movable member engaging the infusion set slide member.

The exemplary embodiments of the present invention described below and shown in FIGS. 1-52 provide a means of performing an intradermal needle insertion at an angle relative to a skin surface via a user motion in which the angle of user motion is different from the insertion angle of the needle. The insertion precisely targets the upper 3 mm of skin surface, and delivers insulin to the intradermal layers of skin via a standard insulin pump (not shown).

Figure 4:
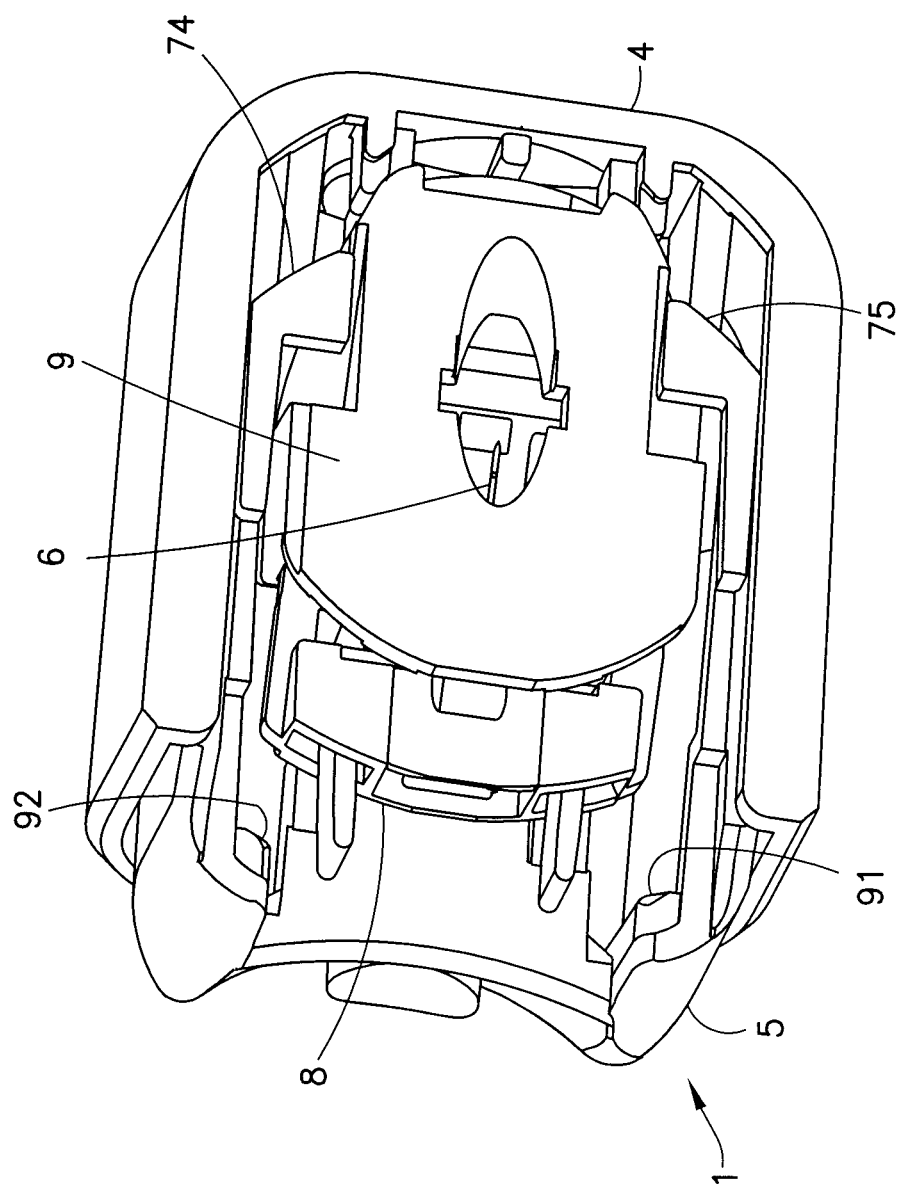
FIG. 4 is a lower perspective view of the infusion set without an adhesive patch and inserter of FIG. 1.
Figure 5:
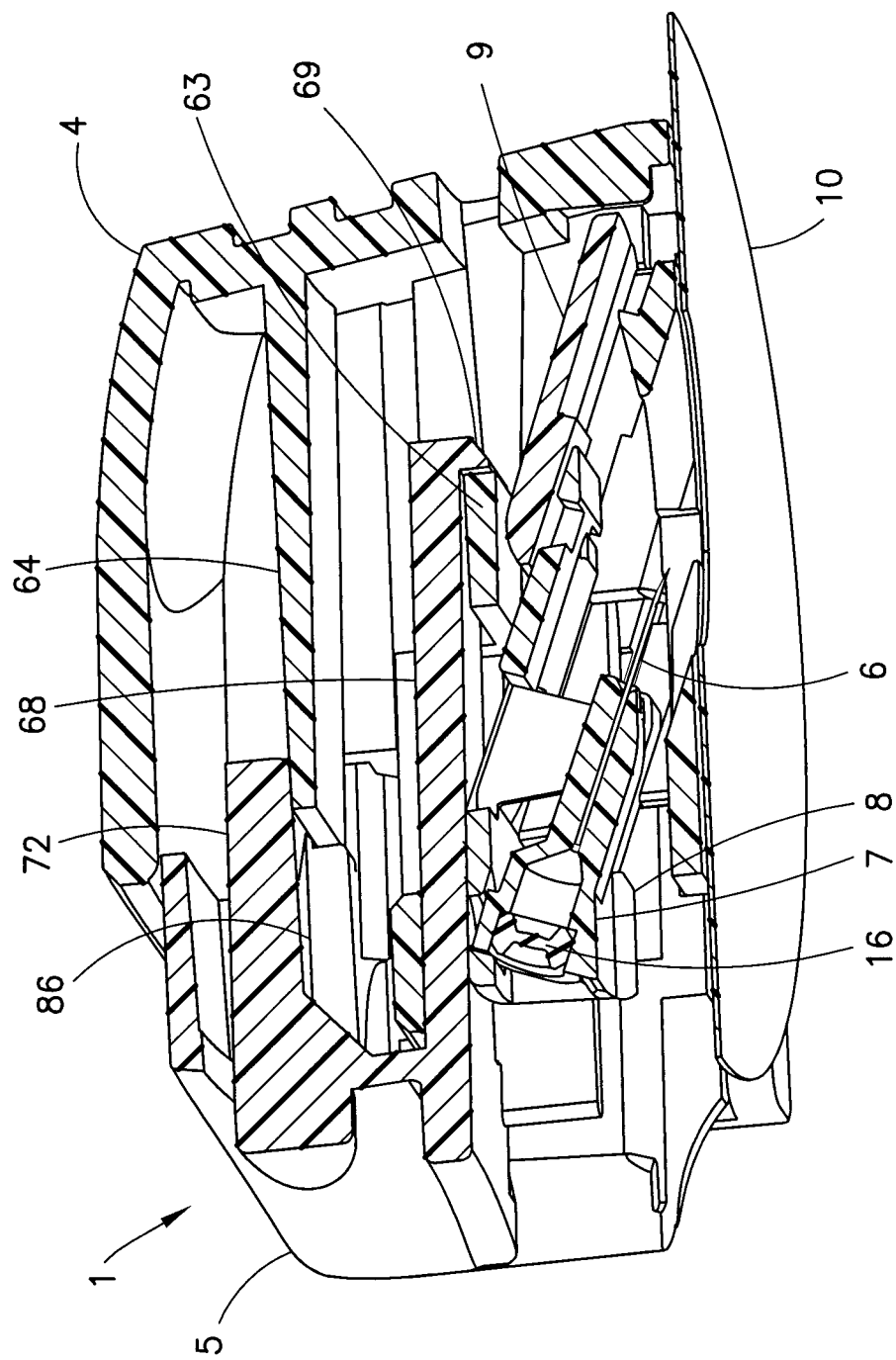
FIG. 5 is a perspective view in cross-section of the infusion set and inserter of FIG. 1 prior to activation.
Figure 6:
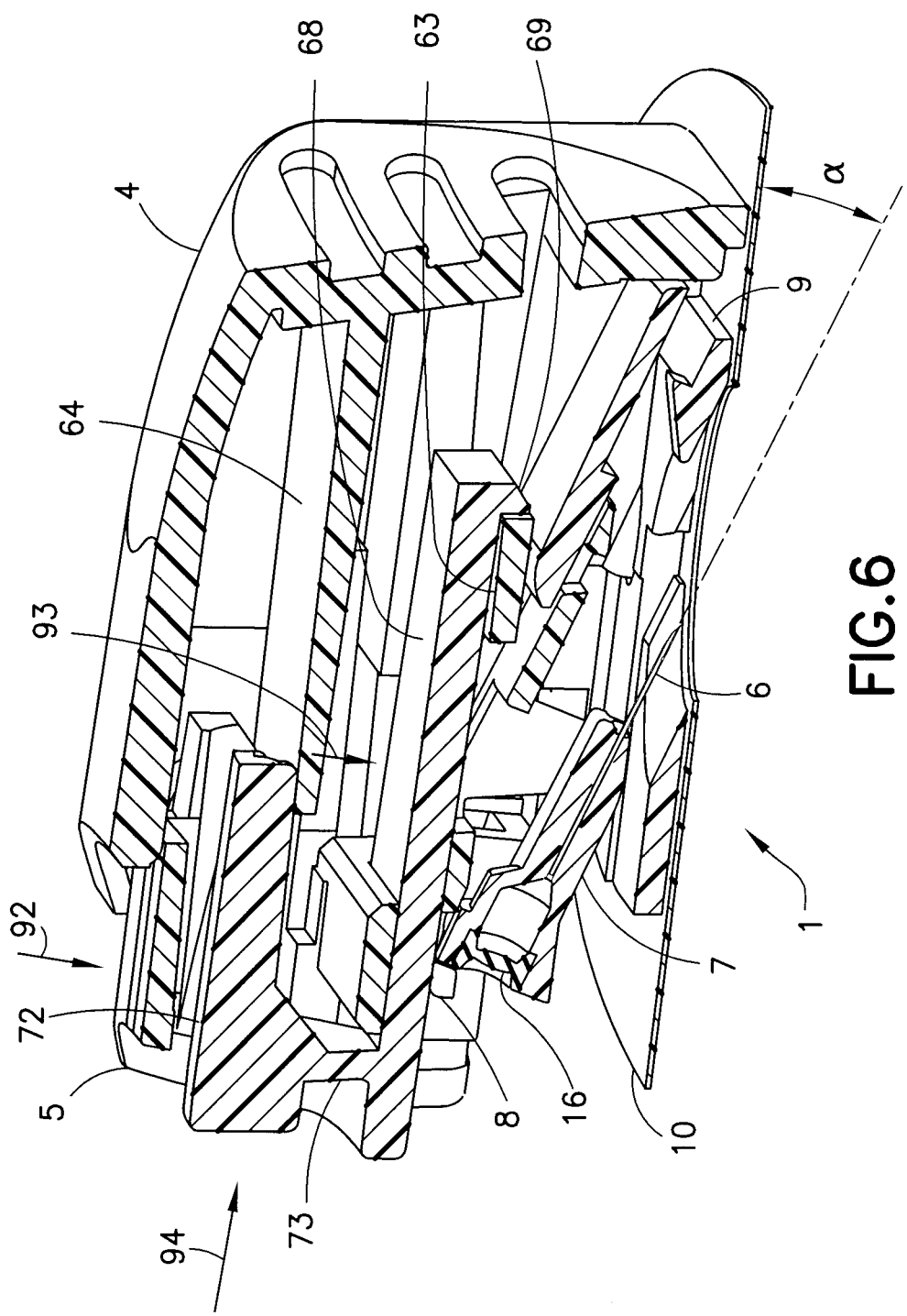
FIG. 6 is a perspective view in cross-section of the infusion set and inserter of FIG. 1 prior to activation.
Figure 10:
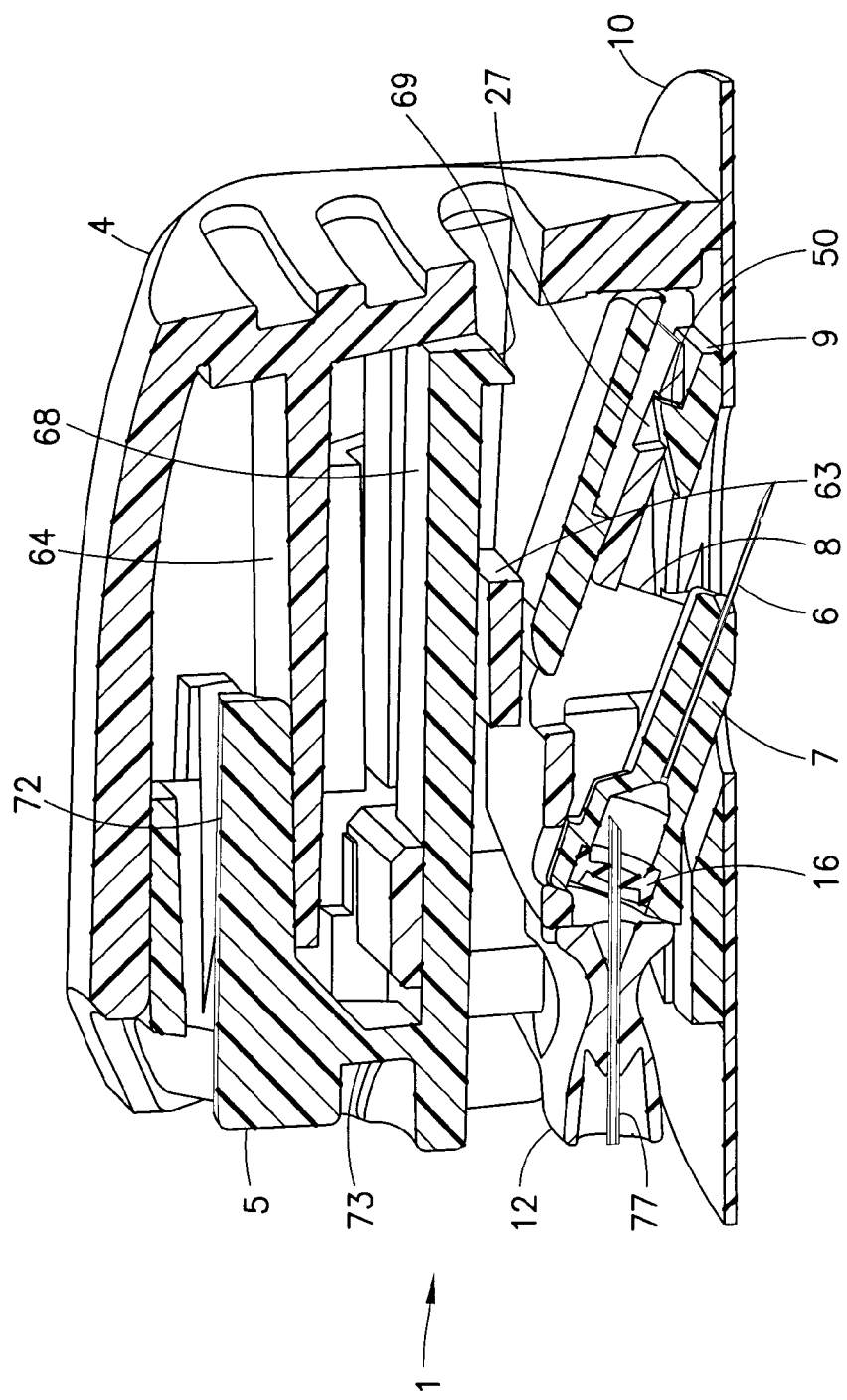
FIG. 10 is a perspective view in cross-section of the infusion set and inserter after insertion of the cannula.

For example, FIGS. 6 and 10 illustrate an infusion set assembly 1 and motion to insert a needle 6 via a user motion in a first direction (indicated by arrow 94 in FIGS. 6 and 7) relative to a skin surface that is different from a second direction (indicated by the angle α in FIGS. 6 and 7) of the inserted needle in accordance with an exemplary embodiment of the present invention. FIGS. 4-6 illustrate an infusion set assembly 1 in a free state before use. FIG. 10 illustrates the infusion set assembly 1 during insertion into the skin surface at an angle relative thereto via a user motion occurring at an angle to the skin surface that is different from the needle insertion angle, in accordance with an exemplary embodiment of the present invention.

Figure 14:
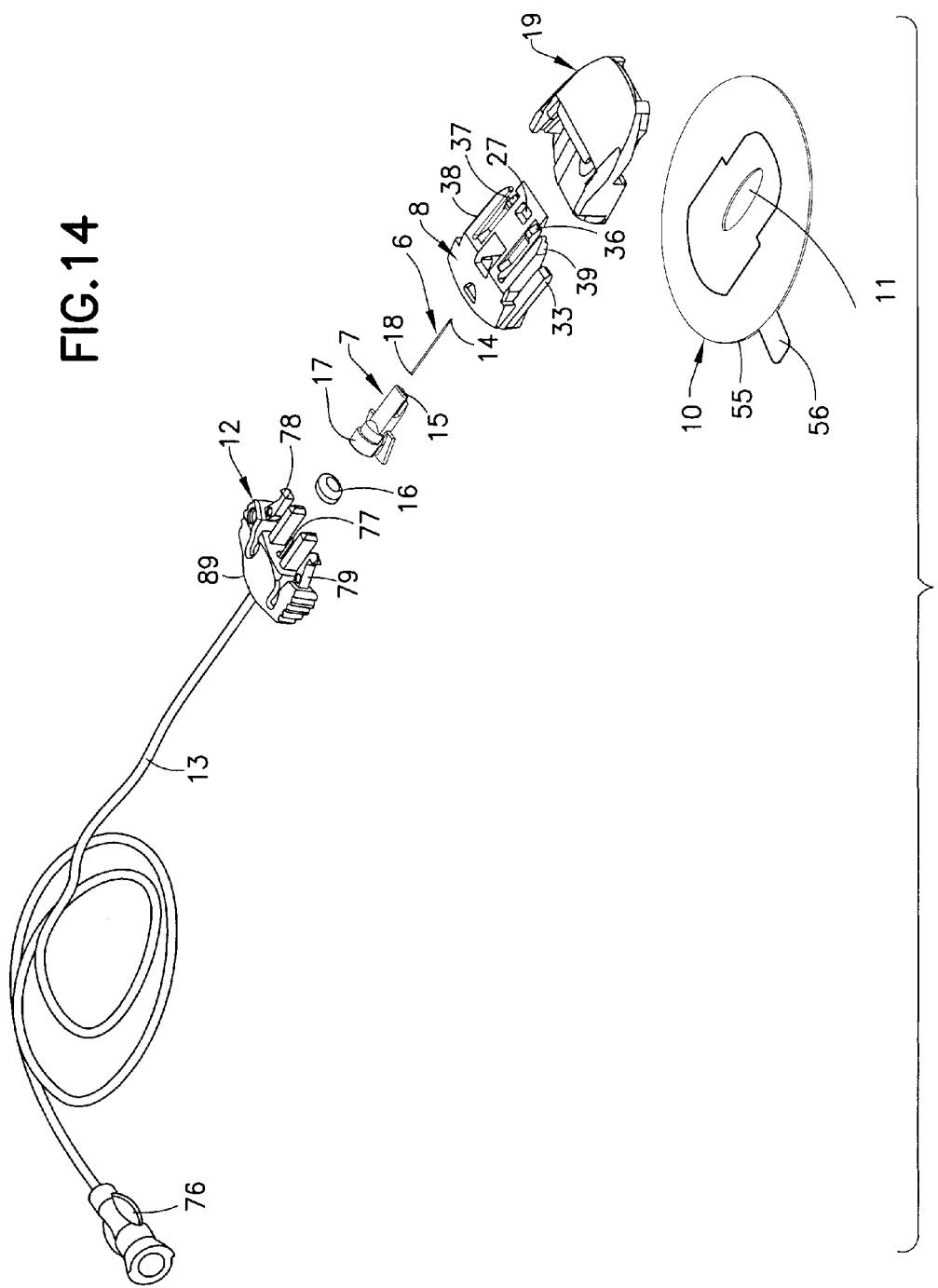
FIG. 14 is an exploded perspective view of the infusion set of FIG. 13.
Figure 15:
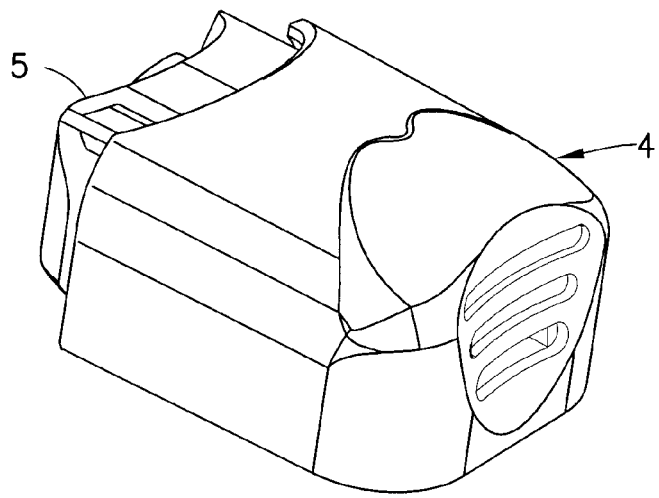
FIG. 15 is a perspective view of an inserter of FIG. 1.
Figure 16:
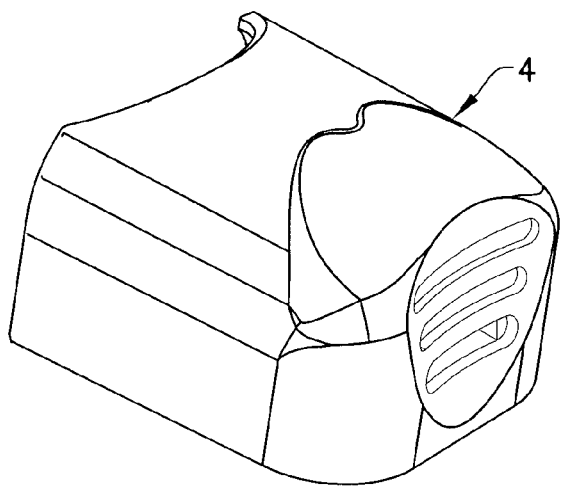
FIG. 16 is a perspective view of a stationary member of the inserter of FIG. 15.
Figure 17:
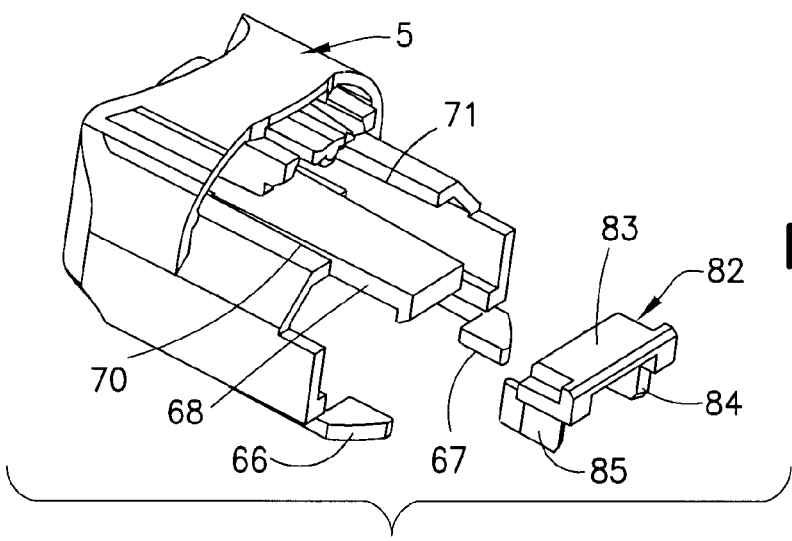
FIG. 17 is an exploded perspective view of a movable member of the inserter of FIG. 15.
Figure 18:
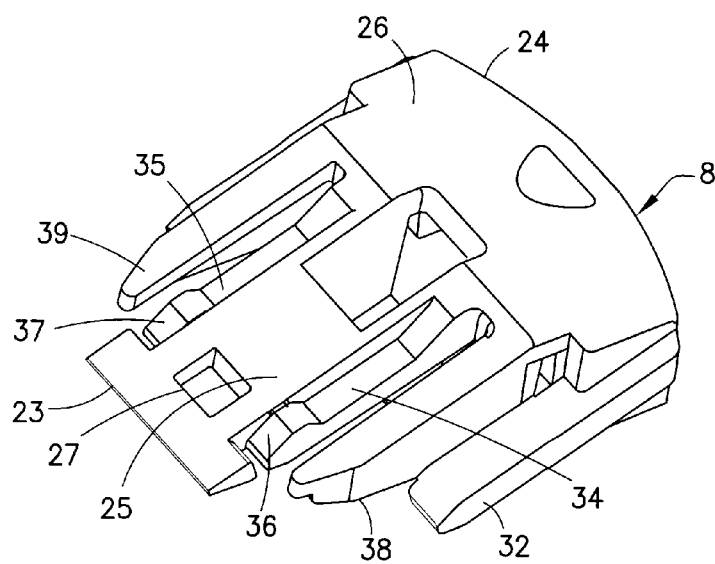
FIG. 18 is a perspective view of a slide of the infusion set of FIG. 13.
Figure 19:
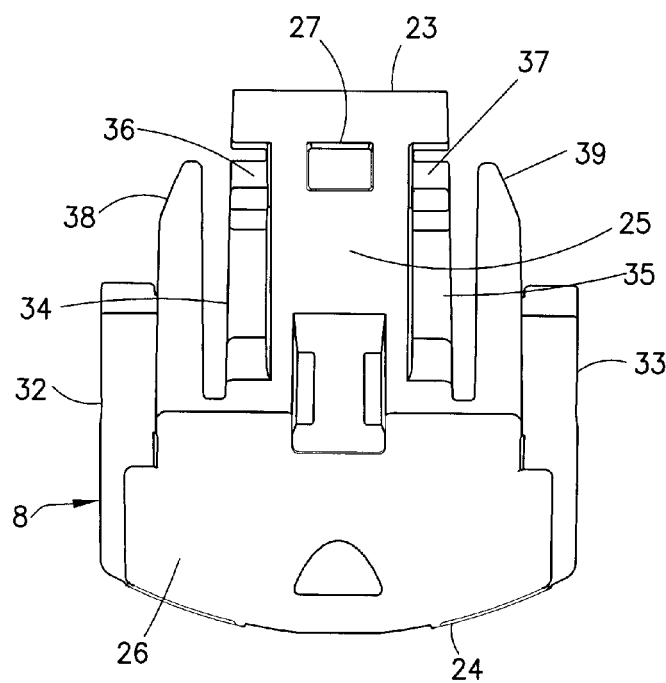
FIG. 19 is a top plan view of the slide of FIG. 18.
Figure 20:
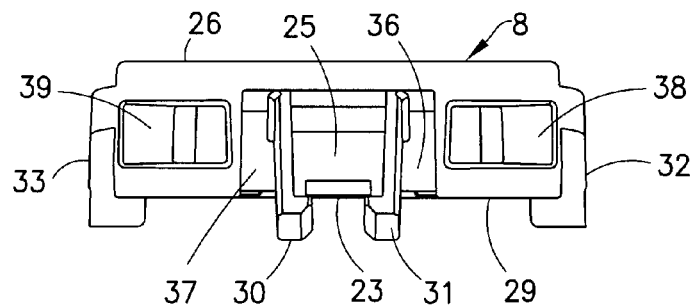
FIG. 20 is a front elevation view of the slide of FIG. 18.
Figure 21:
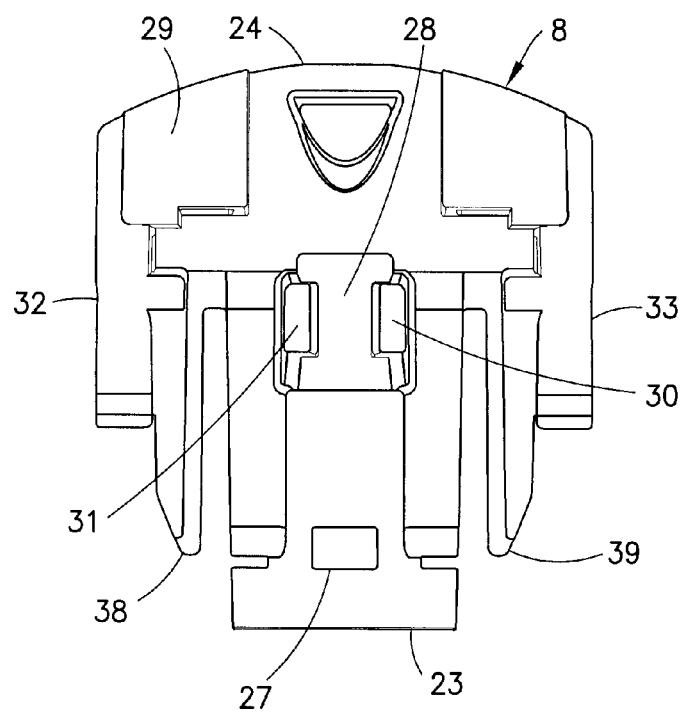
FIG. 21 is a bottom plan view of the slide of FIG. 18.
Figure 22:
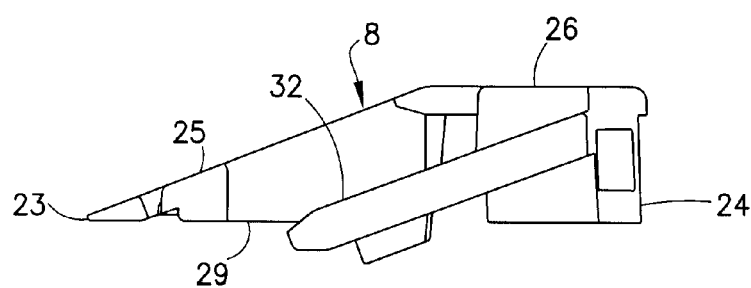
FIG. 22 is a side elevational view of the slide of FIG. 18.
Figure 23:
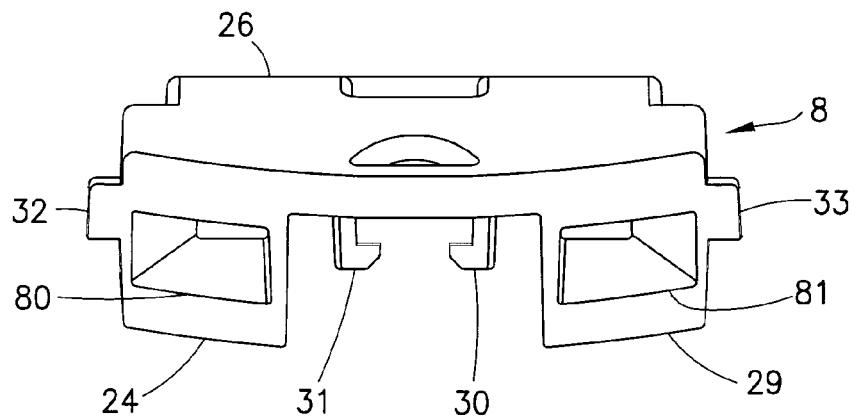
FIG. 23 is a rear elevational view of the slide of FIG. 18.
Figure 24:
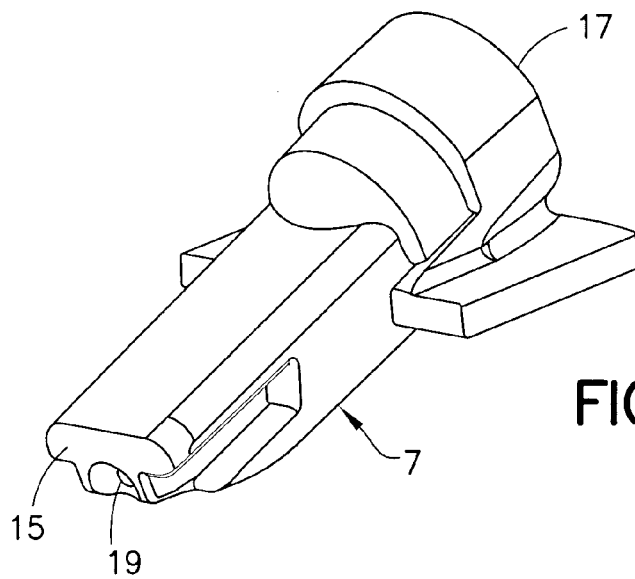
FIG. 24 is a perspective view of a hub of the infusion set of FIG. 13.
Figure 25:
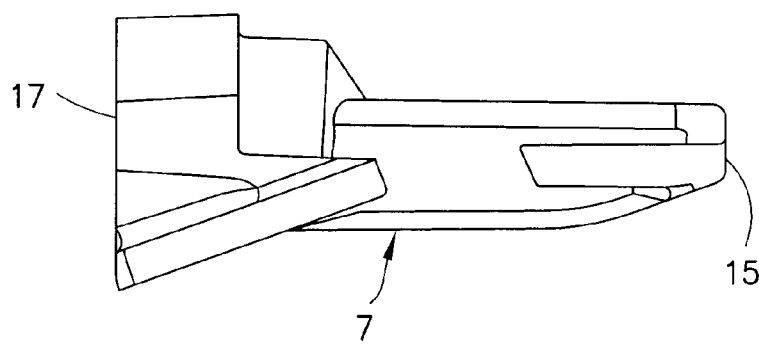
FIG. 25 is a side elevational view of the hub of FIG. 24.
Figure 28:
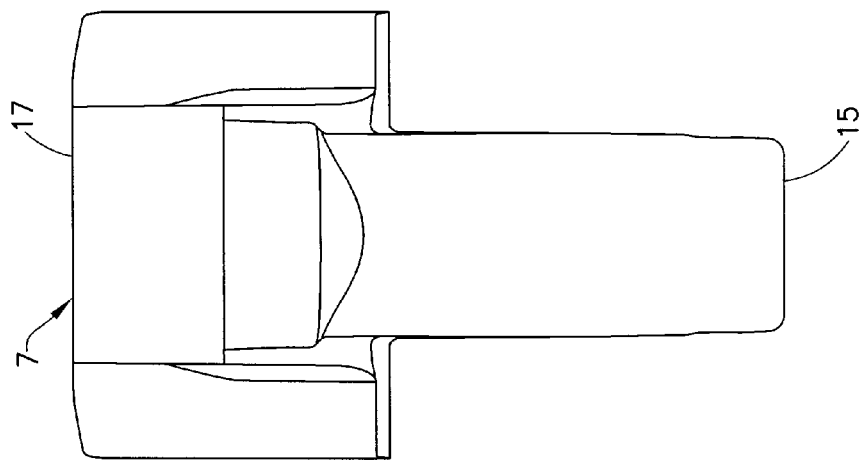
FIG. 28 is a top plan view of the hub of FIG. 24.
Figure 26:
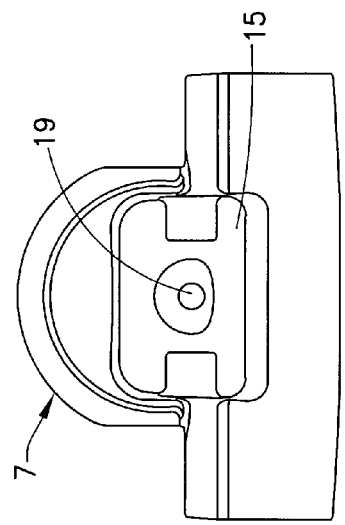
FIG. 26 is a front elevational view of the hub of FIG. 24.
Figure 27:
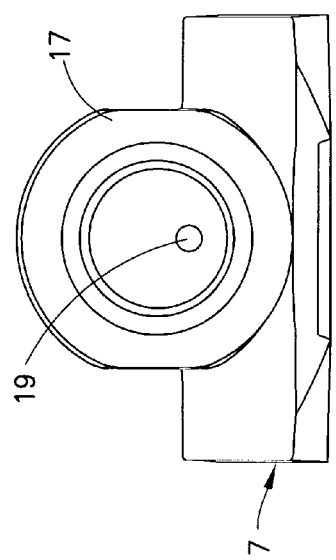
FIG. 27 is a rear elevational view of the hub of FIG. 24.
Figure 29:
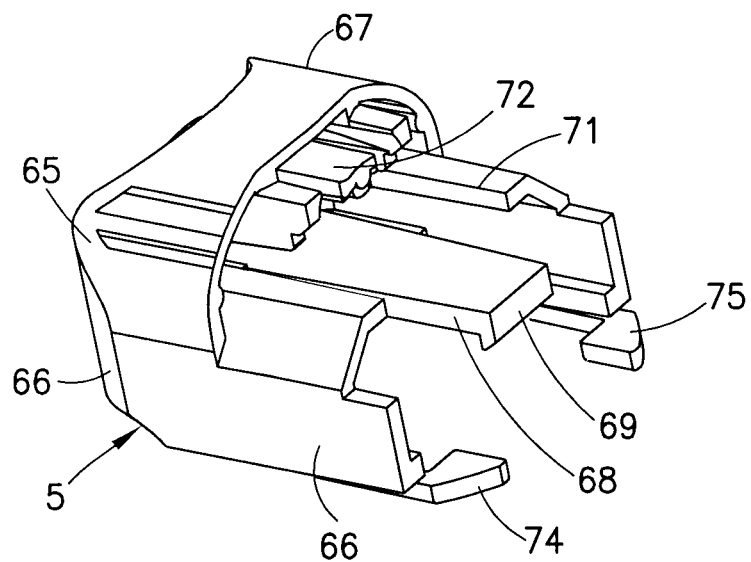
FIG. 29 is a perspective view of a movable member of the inserter of FIG. 1.
Figure 30:
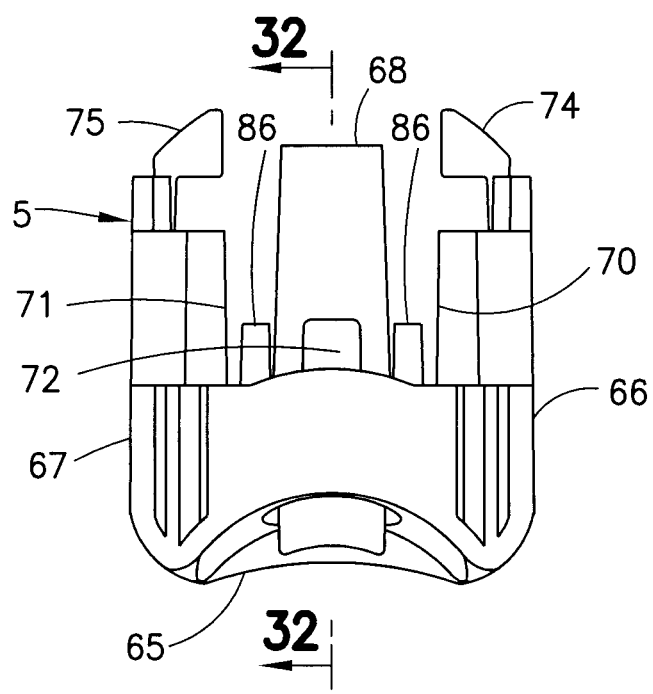
FIG. 30 is a top plan view of the movable member of the inserter of FIG. 29.
Figure 31:
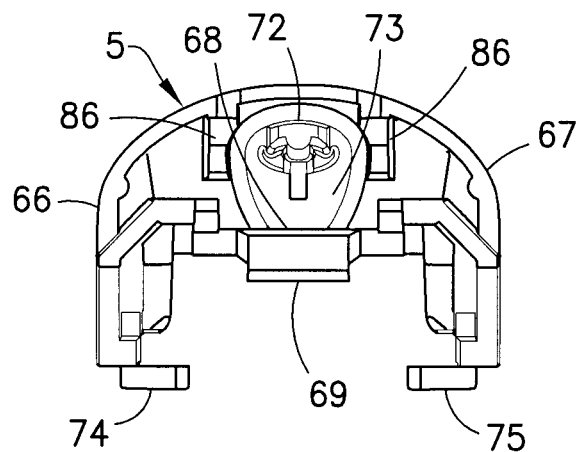
FIG. 31 is a rear elevational view of the movable member of the inserter of FIG. 29.
Figure 32:
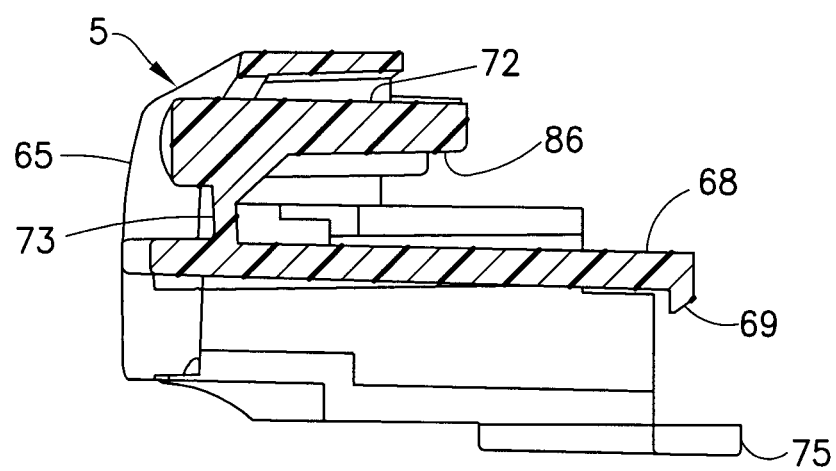
FIG. 32 is a side elevational view in cross-section of the movable member of the inserter of FIG. 29.
Figure 33:
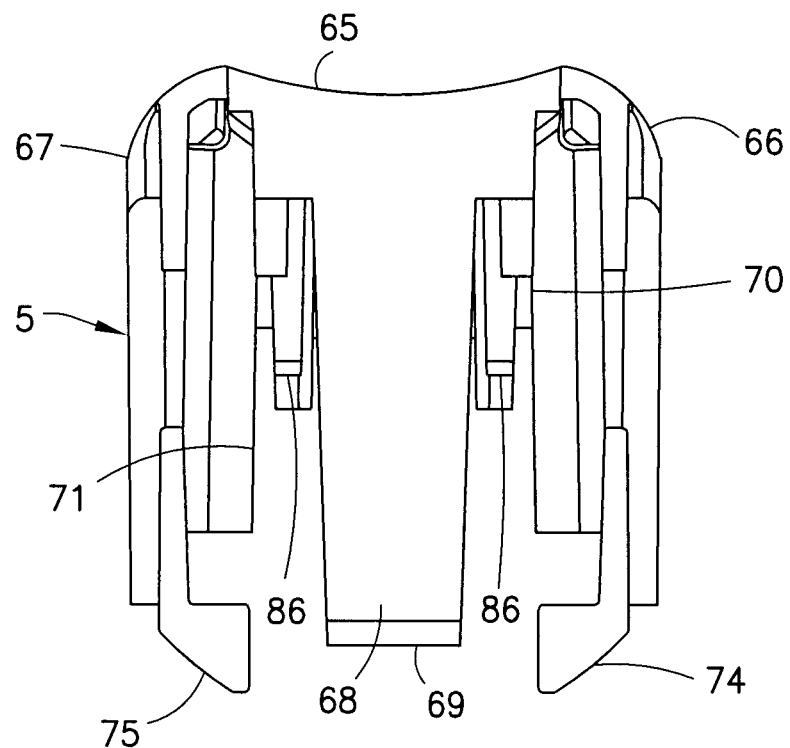
FIG. 33 is a bottom plan view of the movable member of the inserter of FIG. 29.
Figure 34:
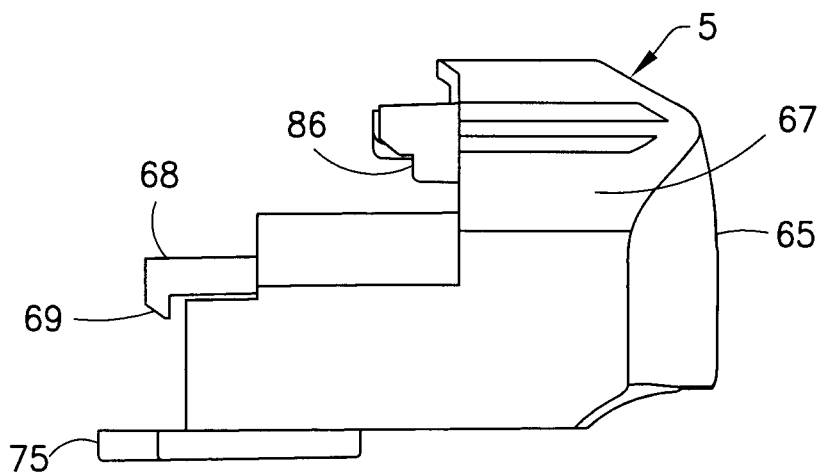
FIG. 34 is a side elevational view of the movable member of the inserter of FIG. 29.
Figure 35:
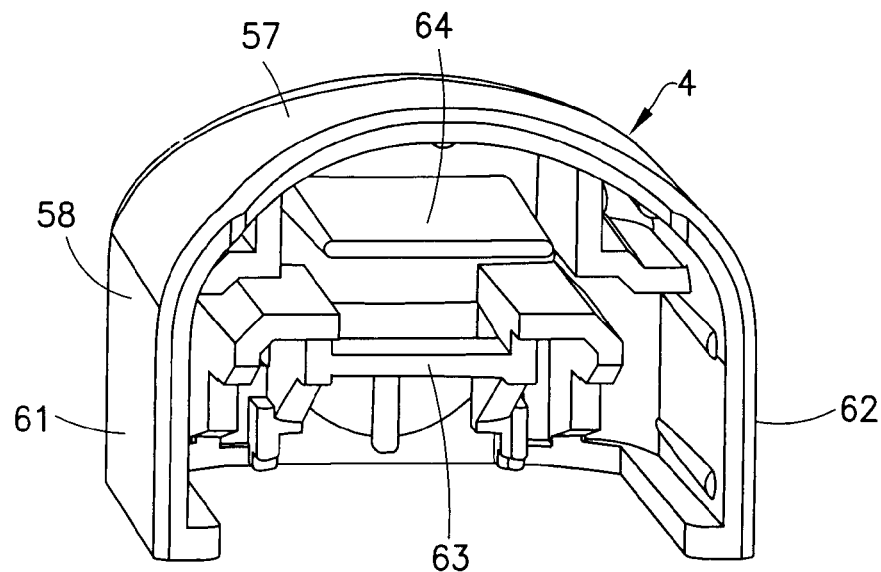
FIG. 35 is a perspective view of a stationary member of the inserter of FIG. 1.
Figure 36:
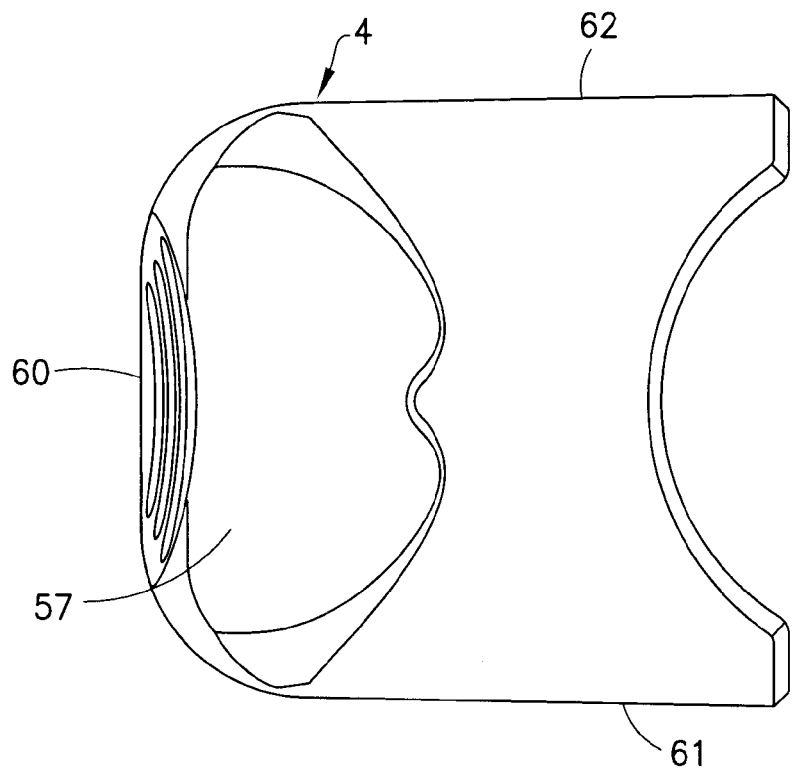
FIG. 36 is a top plan view of the stationary member of the inserter of FIG. 35.
Figure 37:
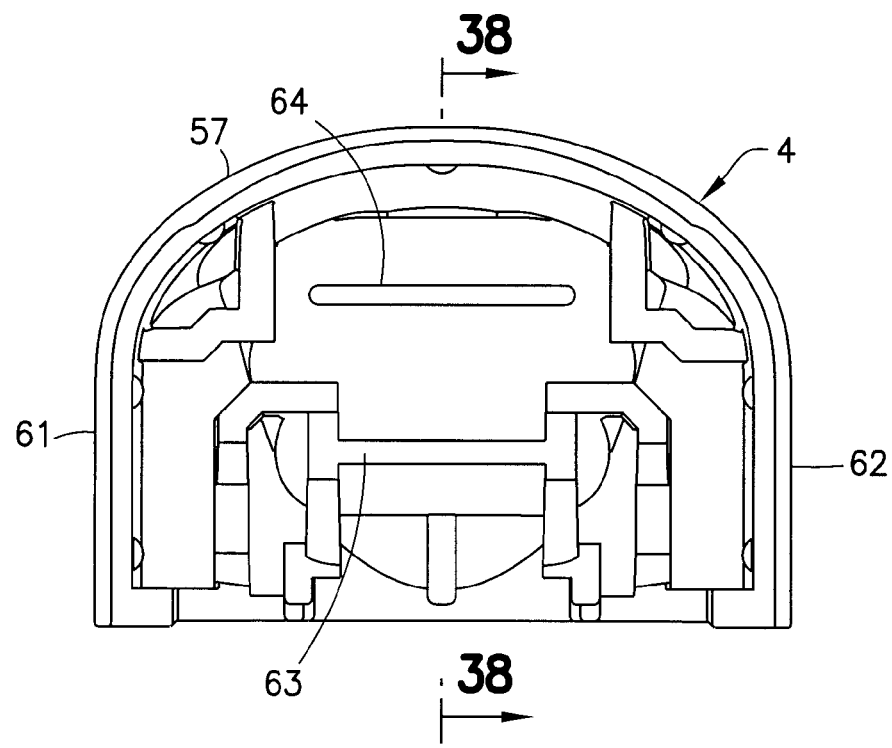
FIG. 37 is a rear elevational view of the stationary member of the inserter of FIG. 35.
Figure 38:
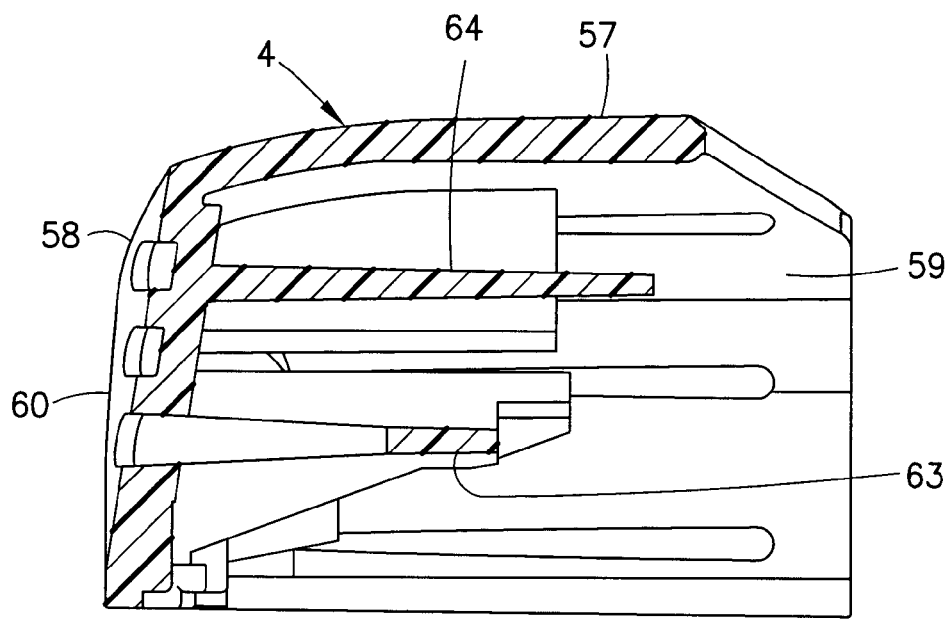
FIG. 38 is a side elevational view in cross-section of the stationary member of the inserter of FIG. 35.
Figure 39:
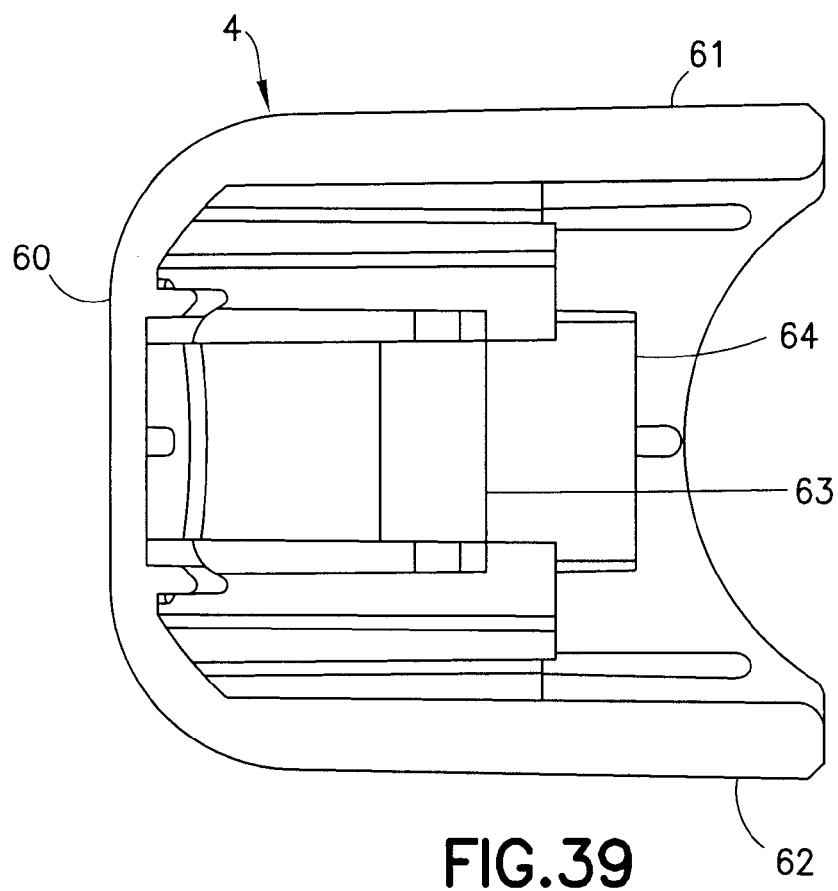
FIG. 39 is a bottom plan view of the stationary member of the inserter of FIG. 35.
Figure 40:
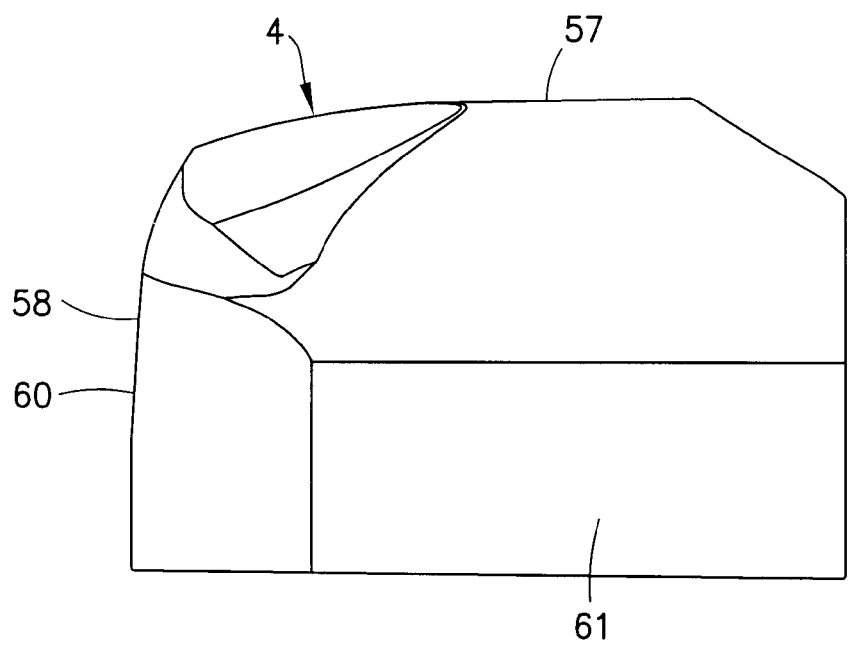
FIG. 40 is a side elevational view of the stationary member of the inserter of FIG. 35.
Figure 41:
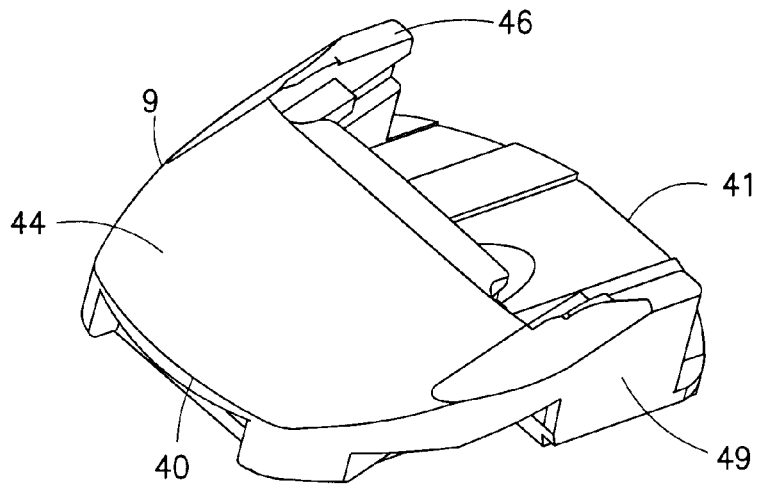
FIG. 41 is a perspective view of a base of the inserter of FIG. 14.

An infusion set assembly 1, as shown in FIG. 1, includes an inserter 2 and an infusion set 3. The inserter 2 includes a fixed inserter member 4 and a movable inserter member 5 movably connected to the fixed inserter member 4. The movable inserter member 5 is movable from a first position shown in FIG. 5 to a second position shown in FIG. 10. The infusion set 3 includes a rigid needle 6, a hub 7, a movable slide member 8 and a fixed base member 9, as shown in FIG. 14. An adhesive pad or patch 10 secures the base member 9 to the skin surface. The rigid needle 6 is fixedly connected to the hub 7, which is fixedly connected to the slide member 8. The slide member 8 moves relative to the fixed base member 9 from a first position in which the needle 6 is not exposed externally of the infusion set 3 to a second position in which the needle 6 is exposed externally of the infusion set 3. An opening 11 in the adhesive pad 10 allows the needle 6 to pass therethrough. A connector 12 connects tubing from an infusion pump (not shown) to the infusion set 3.

The rigid needle 6 is preferably hollow to facilitate delivering medicament therethrough and is preferably made of 31 gauge stainless steel with a sharp beveled tip. An end port in a patient end of the needle 6 allows the medicament to be delivered into the infusion site. A side port can be used in addition to or instead of the end port. An opening in the non-patient end of the needle 6 receives medicament delivered from the insulin pump through tubing 13.

The hub 7, as shown in FIGS. 26-30, fixedly receives the needle 6, which can be secured thereto in any suitable manner, such as with an adhesive. A bore 19 in the hub 7 receives the needle 6, which can be secured therein with an adhesive. The patient end 14 of the needle 6 extends beyond a first end 15 of the hub 7. A septum 16 is disposed in a second end 17 of the hub 7 to seal the hub and prevent access to the opening in the non-patient end 18 of the needle 6. The septum 16 is preferably made of isoprene, but any suitable material can be used. The hub 7 is preferably made of an injection-molded plastic, although any suitable material can be used.

The slide member 8, as shown in FIGS. 18-23, has a front end 23 and a rear end 24. An angled portion 25 of an upper surface 26 slopes upwardly from the front end 23 toward the rear end 24. Preferably, the angled portion 25 has an angle of between approximately ten (10) and forty-five degrees (45), inclusive. More preferably, the angled portion has an angle of approximately twenty (20) degrees. An opening 27 is formed in the angled portion 25 of the upper surface 26. A cavity 28 is formed in a lower surface 29 of the slide member 8 to receive the hub 7. Flex arms 30 and 31 extend outwardly from the lower surface 29 proximal the cavity 28 to facilitate securing the hub 7 in the cavity 28. Preferably, the hub 7 is secured at an angle substantially similar to the angle of the angled portion 25. Outer rails 32 and 33 extend outwardly from opposite sides of the slide member 8. Preferably, the outer rails 32 and 33 are disposed at an angle substantially similar to that of the angled portion 25. Snap arms 34 and 35 are disposed inwardly of the outer rails 32 and 33. Hooks 36 and 37 extend upwardly from ends of the snap arms 34 and 35. Stop arms 38 and 39 are disposed between the outer rails 32 and 33 and the snap arms 34 and 35, respectively. Openings 80 and 81 in the rear end 24 receive connector arms 78 and 79 (FIG. 14) to secure the connector 12 thereto. The slide member 8 is preferably made of an injection-molded plastic, such as PETG, but any suitable material can be used.

Figure 42:
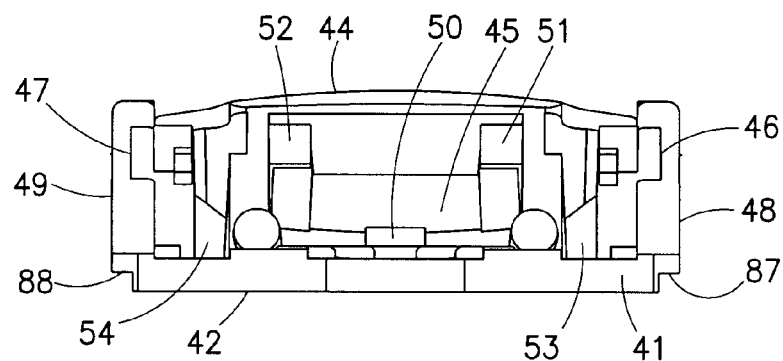
FIG. 42 is a rear elevational view of the base of FIG. 41.
Figure 43:
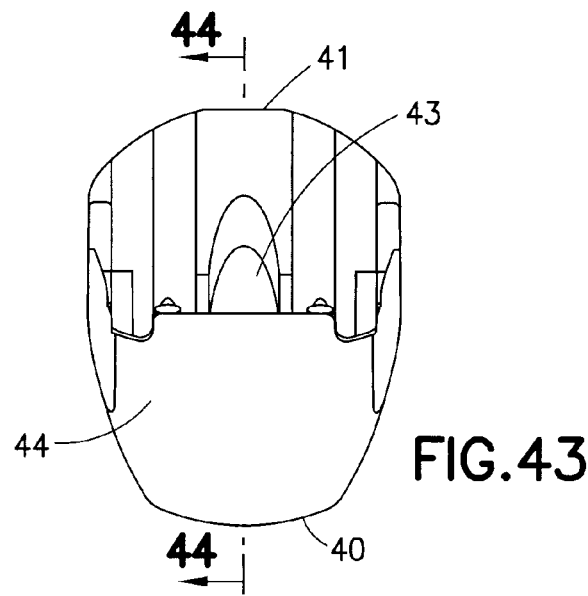
FIG. 43 is a bottom plan view of the base of FIG. 41.
Figure 44:
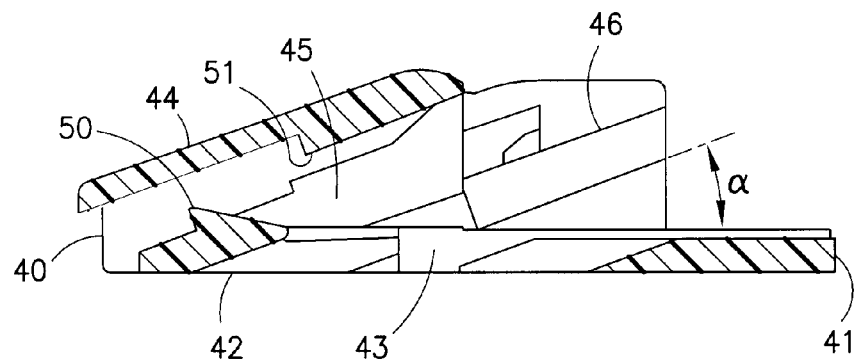
FIG. 44 is a side elevational view in cross-section of the base of FIG. 41.
Figure 45:
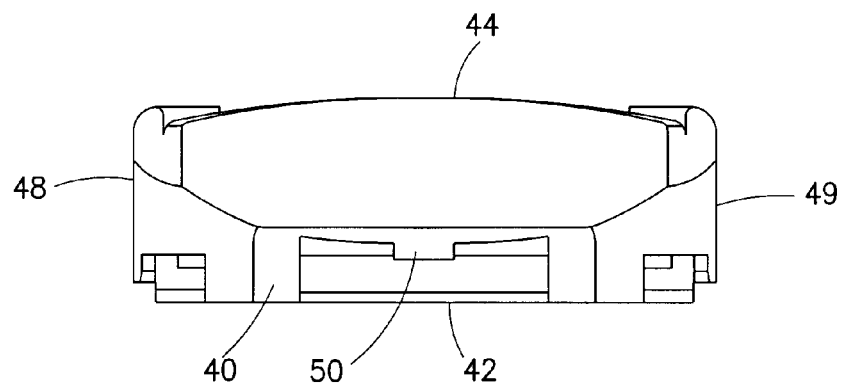
FIG. 45 is a front elevational view of the base of FIG. 41.
Figure 46:
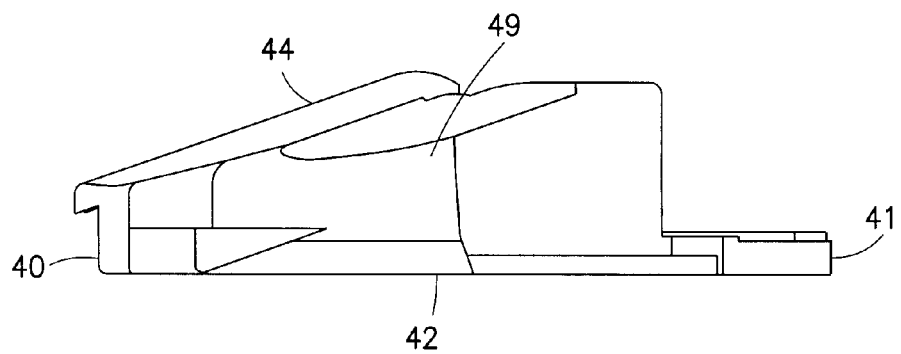
FIG. 46 is a side elevational view of the base of FIG. 41.

The base member 9, as shown in FIGS. 41-46, has a front end 40 and a rear end 41. A lower surface 42 extends from the front end 40 toward the rear end 41. An opening 43 in the lower surface 42 allows the needle 6 to pass therethrough. Preferably, the opening 43 has a substantially oval shape. An upper surface 44 extends rearwardly from the front end 40 and defines a cavity 45 between the supper surface 44 and the lower surface 42 for receiving the slide member 8. Outer channels 46 and 47 are formed in side walls 48 and 49 extending between the lower surface 42 and the upper surface 44. A lower tab 50 extends upwardly from the lower surface 42, as shown in FIG. 44. Upper tabs 51 and 52 extend downwardly from the upper surface 44, as shown in FIGS. 42 and 44. Inner channels 53 and 54 are disposed between upper tabs 51 and 52 and the channels 46 and 47. The base member 9 is preferably made of an injection-molded plastic, such as PETG, but any suitable material can be used.

Figure 3:
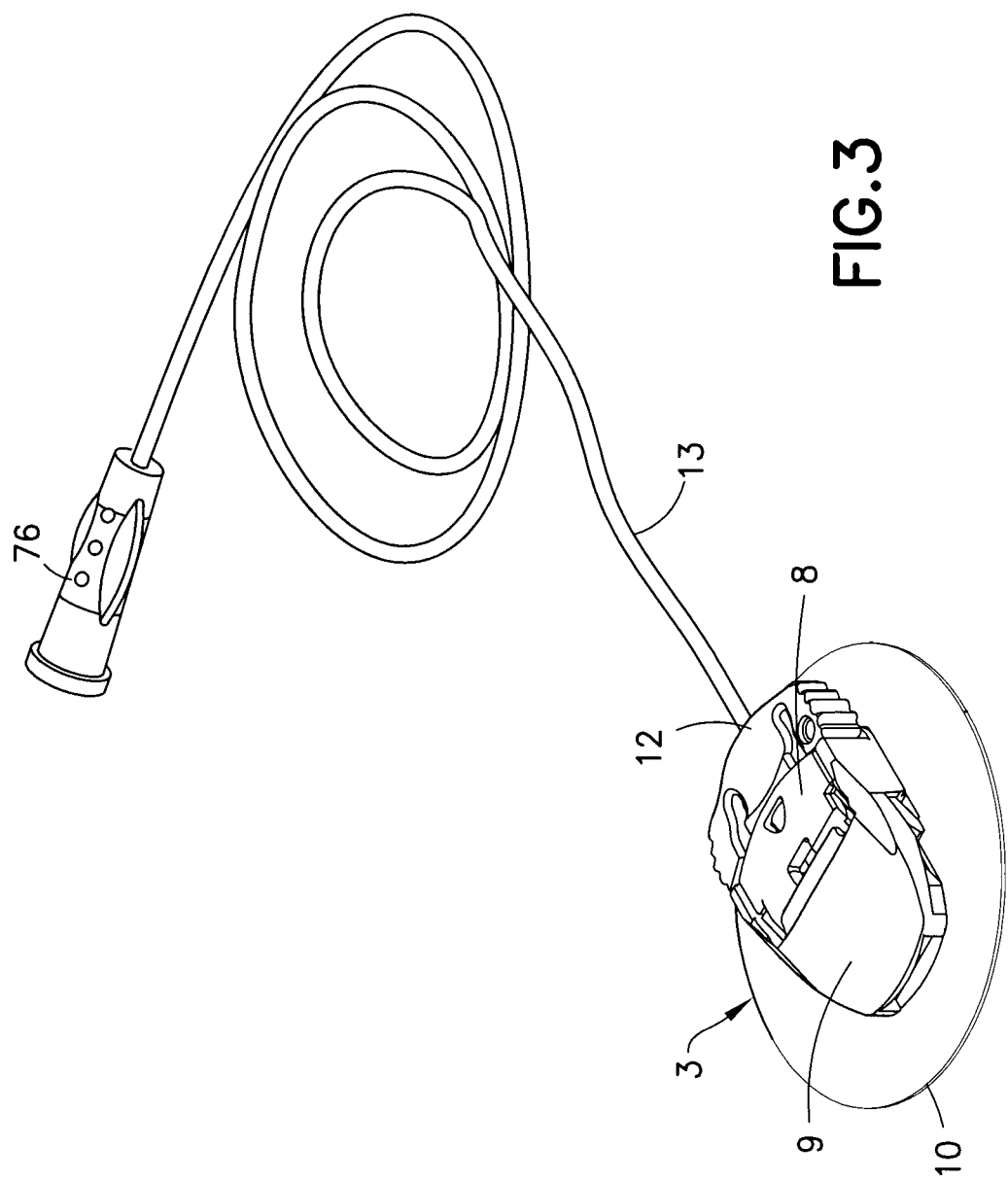
FIG. 3 is a perspective view of the infusion set of FIG. 1 after removal of the inserter.

A pressure sensitive adhesive pad 10 is connected to the lower surface 42 of the base member 9, as shown in FIGS. 1, 3 and 14. An adhesive backing 55 is connected to the adhesive pad 10 to cover the adhesive pad prior to use. The adhesive backing 55 has a tab element 56 to facilitate separating the cover from the adhesive pad 10 to expose the adhesive pad when the adhesive pad is to be secured to an infusion site. The pressure sensitive adhesive pad 10 can comprise any suitable material, such as an adhesive fabric.

The fixed inserter member 4 has an upper surface 57 with a wall 58 extending downwardly therefrom, as shown in FIGS. 35-40. The upper surface 57 and the wall 58 define a cavity 59. Preferably, the wall 58 has a front wall 60 and opposing side walls 61 and 62 with a rear portion thereof being open to provide access to the cavity 59. A shelf 63 disposed in the cavity 59 extends laterally between the side walls 61 and 62. A flexible beam 64 extends rearwardly from the front wall 60 in the cavity 59. The fixed inserter member 4 is preferably made of an injection-molded plastic, such as acrylonitrile butadiene styrene (ABS), but any suitable material can be used.

The movable inserter member 5 has a rear wall 65 and opposing side walls 66 and 67 extending forwardly therefrom, as shown in FIGS. 29-34. A latching arm 68 extends forwardly from the rear wall 65 and has a tab 69 extending downwardly from a free end thereof. Slots 70 and 71 extend parallel to opposite sides of the latching arm 68. A flexible member 72 is preferably connected to the movable inserter member 5 by a living hinge 73, although any suitable means for connecting the flexible member can be used that allows deflection of the flexible member. Locking feet 74 and 75 extend forwardly from side walls 66 and 67. The movable inserter member 5 is preferably made of an injection-molded plastic, such as PETG, but any suitable material can be used.

The connector 12 has flexible plastic tubing 13 connected thereto for delivering medicament from the insulin pump (not shown) to the infusion set 3, as shown in FIG. 14. A pump connector 76 is disposed at one of the tubing 13 for connecting to the insulin pump. The connector 12 is disposed at the other end of the tubing 13 for connecting to the slide member 8 of the infusion set 3. The tubing 13 connects through a rear surface 89 of the connector 12. A needle 77 extends forwardly from the connector 12 to pierce the septum 16 disposed in the hub 7 when the connector 12 is connected to the slide member 8. By piercing the hub septum 16, the hub needle 6 is fluidly connected to the insulin pump. Snap arms 78 and 79 are received by the slide member 8 to secure the connector 12 thereto. Moving the snap arms 78 and 79 inwardly allows the connector 12 to be disconnected from the infusion set 3 as necessary.

A connector tab 82, as shown in FIGS. 17 and 48-51, has a base 83 and legs 84 and 85 extending downwardly from the base 83. The legs 84 and 85 of the connector tab 82 are received by the slots 70 and 71 of the movable inserter member 5 such that the base 83 is disposed above the latching arm 68. Alternatively, the connector tab 82 can be integrally formed with the movable inserter member 5 as a single piece.

Operation and Assembly

The exemplary embodiments comprise an adhesive secured infusion set 3 and a disposable inserter 2 for performing an intradermal needle insertion precisely targeting the upper 3 mm of skin surface. The infusion set 3 can be adhesively attached to a skin surface, and the inserter 2 can be used to angularly insert the needle 6 into a desired insertion position. The insertion position of the needle 6 is maintained by securing the slide member 8 to the base member 9 to hold the inserted needle 6 in position and prevent the slide member 8 and inserted needle 6 from retraction once in the inserted position.

Figure 2:
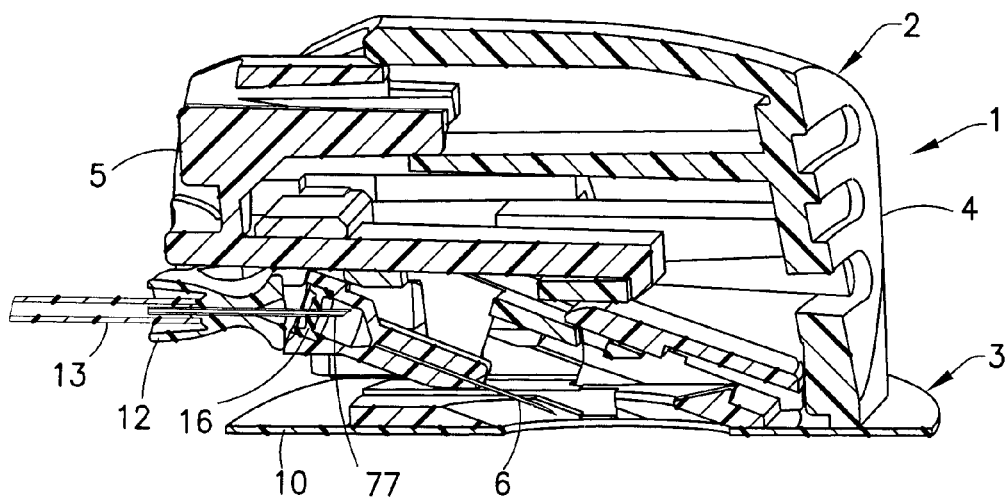
FIG. 2 is an elevational view in cross-section of the infusion set and inserter of FIG. 1.

The infusion set assembly 1 can include a disposable inserter 2, as shown in FIGS. 1 and 2. The inserter 2 can also be reusable if desired. Preferably, the infusion set assembly 1 is packaged such that the infusion set 3 is retained by the inserter 2. Alternatively, the infusion set 3 can be packaged without the inserter 2. The needle 6 is initially slightly recessed in the infusion set 6 to substantially prevent an accidental needle stick, but is visible from a bottom of the infusion set 2, as shown in FIG. 4, so a user can visibly determine priming of the infusion set 3 prior to adhering the infusion set 3 to an infusion site.

The exemplary embodiments are configured to be efficient and user friendly. The user first peels off the adhesive backing 55, revealing the adhesive pad 10 on the lower surface 42 of the base member 9 of the infusion set 3. The infusion set assembly 1 can then be adhered to the infusion site with a downward pressure or application force by the user. The sliding action of the sliding base member 5 angularly inserts the needle 6, as described in greater detail below, into the upper 3 mm of skin surface, the intradermal space, to facilitate better drug absorption. After the needle 6 has been inserted, the inserter 2 can be removed and properly disposed of. The user can disconnect and reconnect the connector 12 as desired.

Figure 47:
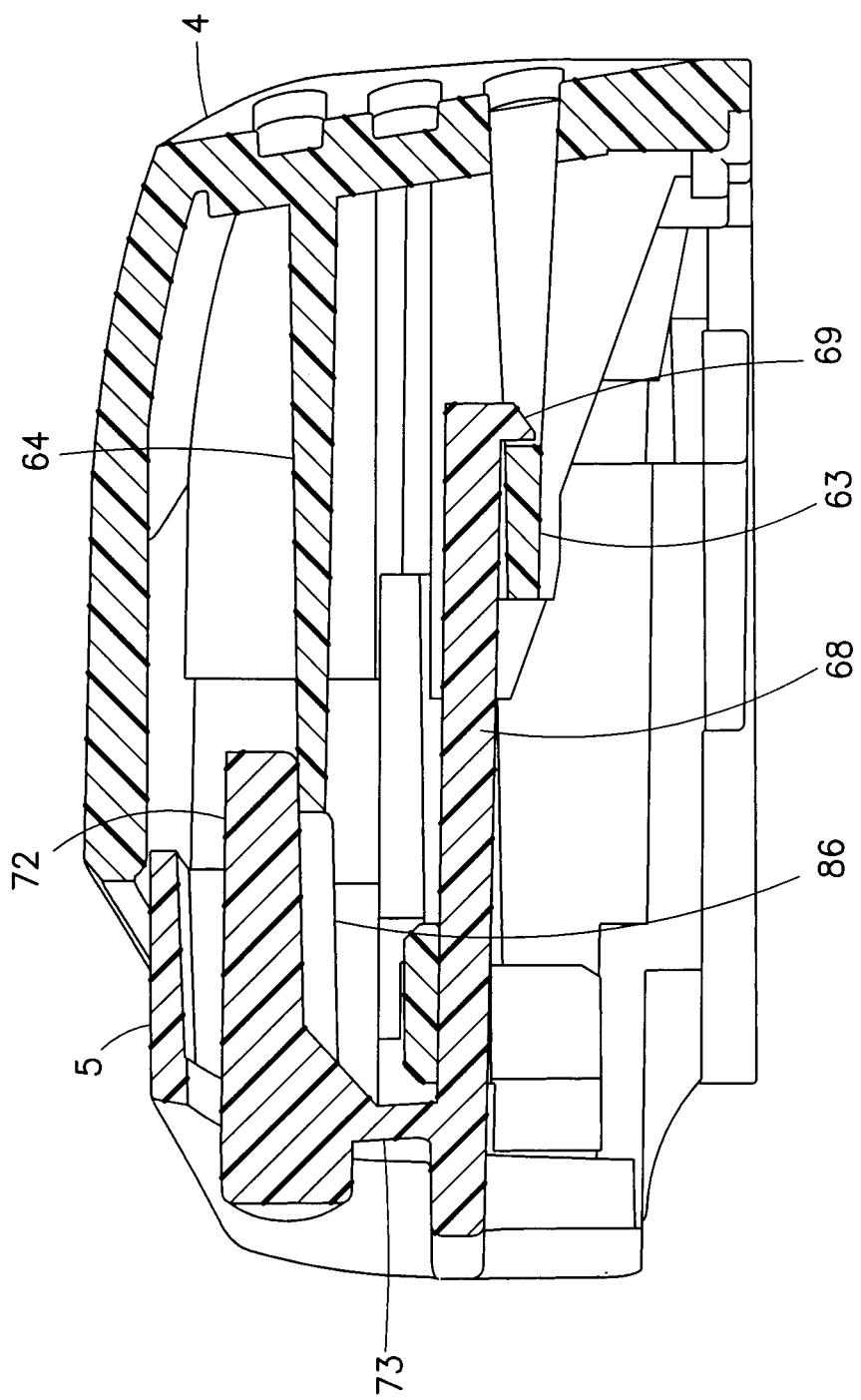
FIG. 47 is an elevational view in cross section of the inserter of FIG. 1.
Figure 48:
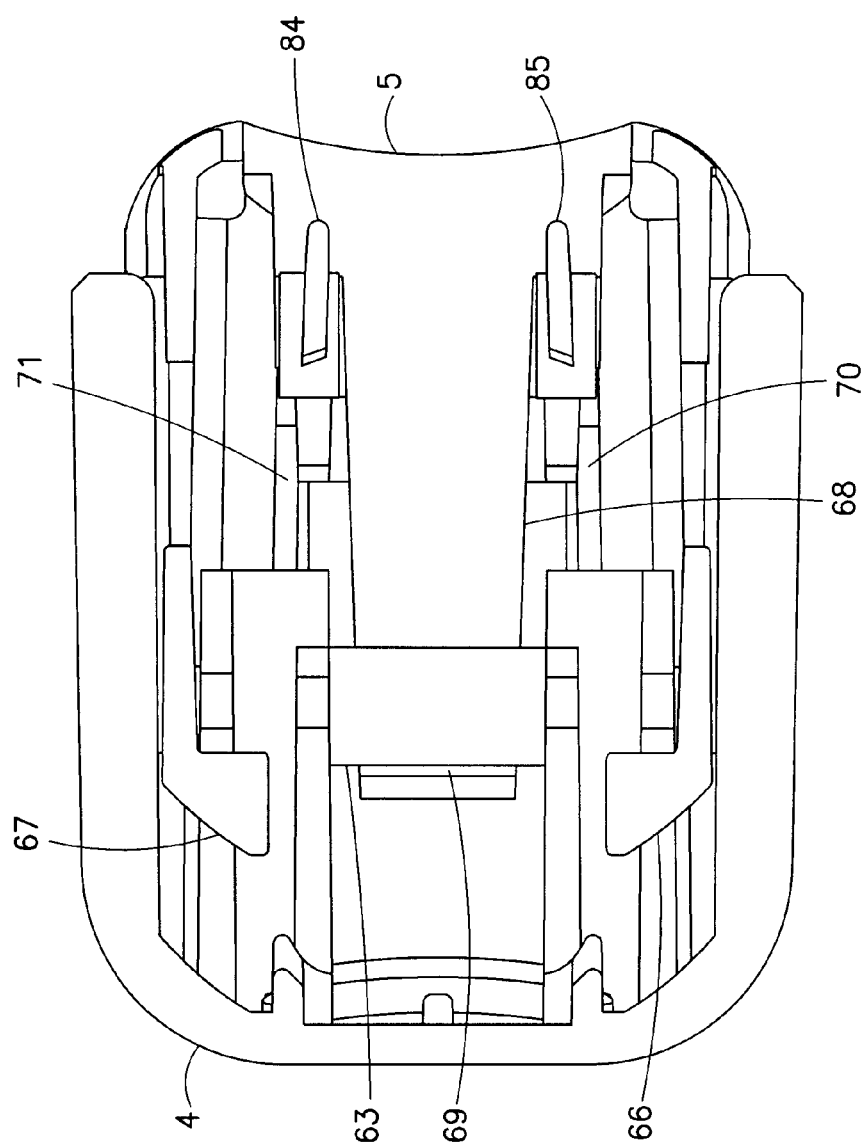
FIG. 48 is a bottom perspective view of the inserter of FIG. 1.
Figure 49:
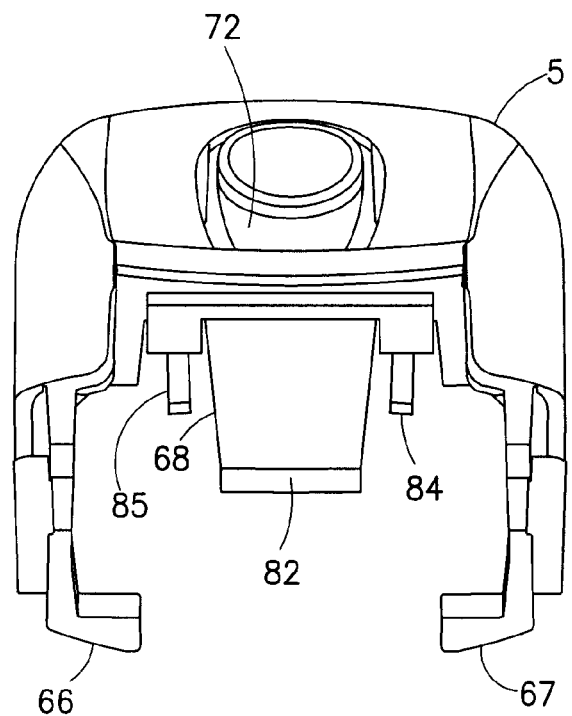
FIG. 49 is a rear perspective view of the movable member of the inserter of FIG. 1.
Figure 50:
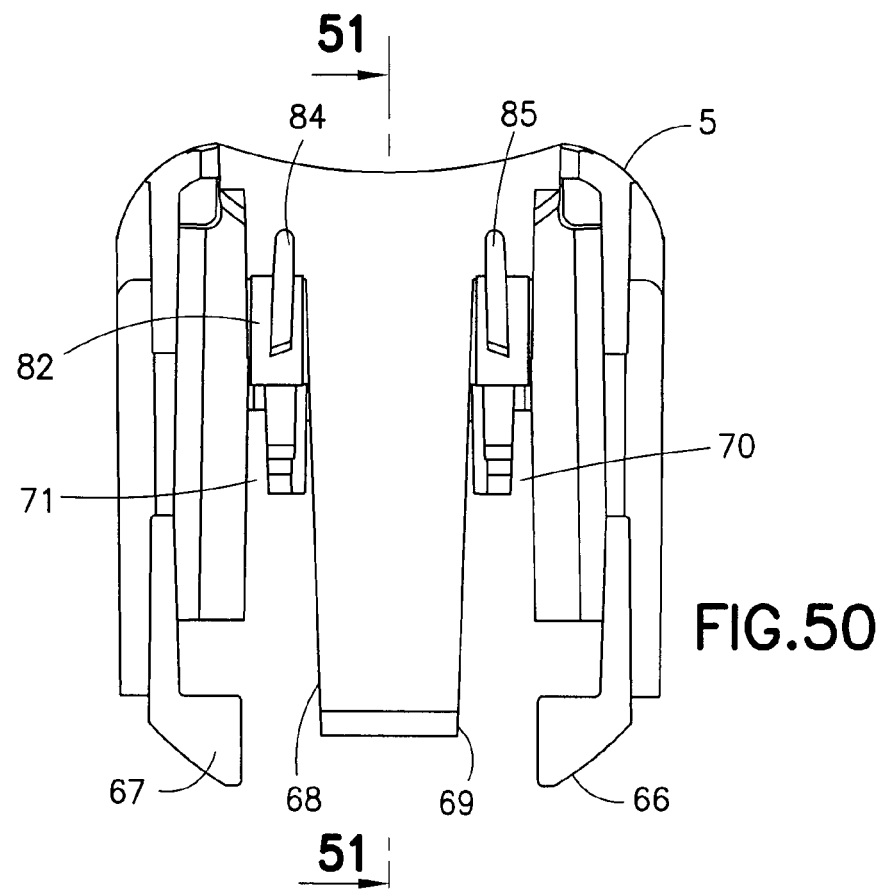
FIG. 50 is a bottom plan view of the movable member of FIG. 49.
Figure 51:
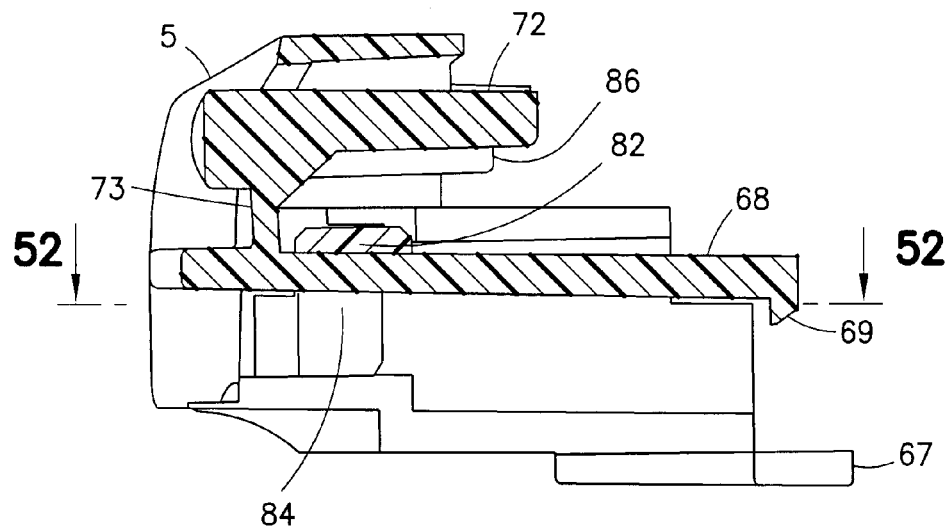
FIG. 51 is an elevational view in cross section of the movable member of FIG. 49.

Prior to activation, the infusion set slide member 8 and the movable inserter member 5 are locked in their first positions, as shown in FIGS. 4-6. As noted above, the needle 6 is recessed within and visible through the openings 11 and 43 in the adhesive pad 10 and the base member 9, respectively, as shown in FIG. 4, thereby preventing accidental needle sticks and allowing for visible priming of the infusion set 3. The tab 69 of the latching arm 68 of the movable inserter member 5 engages the shelf 63 of the fixed inserter member 4, as shown in FIGS. 5, 47 and 48, thereby preventing the movable inserter member from being separated from the fixed inserter member 4. Additionally, prior to activation, the flexible beam 64 of the fixed inserter member 4 engages ribs 86 extending downwardly from the flexible member 72 of the movable inserter member 5, as shown in FIG. 47, thereby preventing accidental activation of the infusion set 3. Accordingly, the movable inserter member 5 is prevented from being withdrawn from the fixed inserter member 4 in addition to being prevented from being moved into the fixed inserter member.

Additionally, the infusion set 3 is prevented from being removed from the inserter 2 prior to activation, as shown in FIG. 4. The locking feet 74 and 75 of the movable inserter member 4 engage longitudinally extending base members 87 and 88 (FIG. 42), thereby preventing removal of the inserter 2 from infusion set 3 prior to fully inserting the needle 6. Inwardly extending retaining ribs 90 and 91 engage the rear surface 89 of the connector 12 to prevent withdrawal of the infusion set 3 from the inserter 2 prior to activation. Accordingly, the infusion set 3 is retained by the inserter 2 prior to activation and until the needle 6 is fully inserted.

Figure 7:
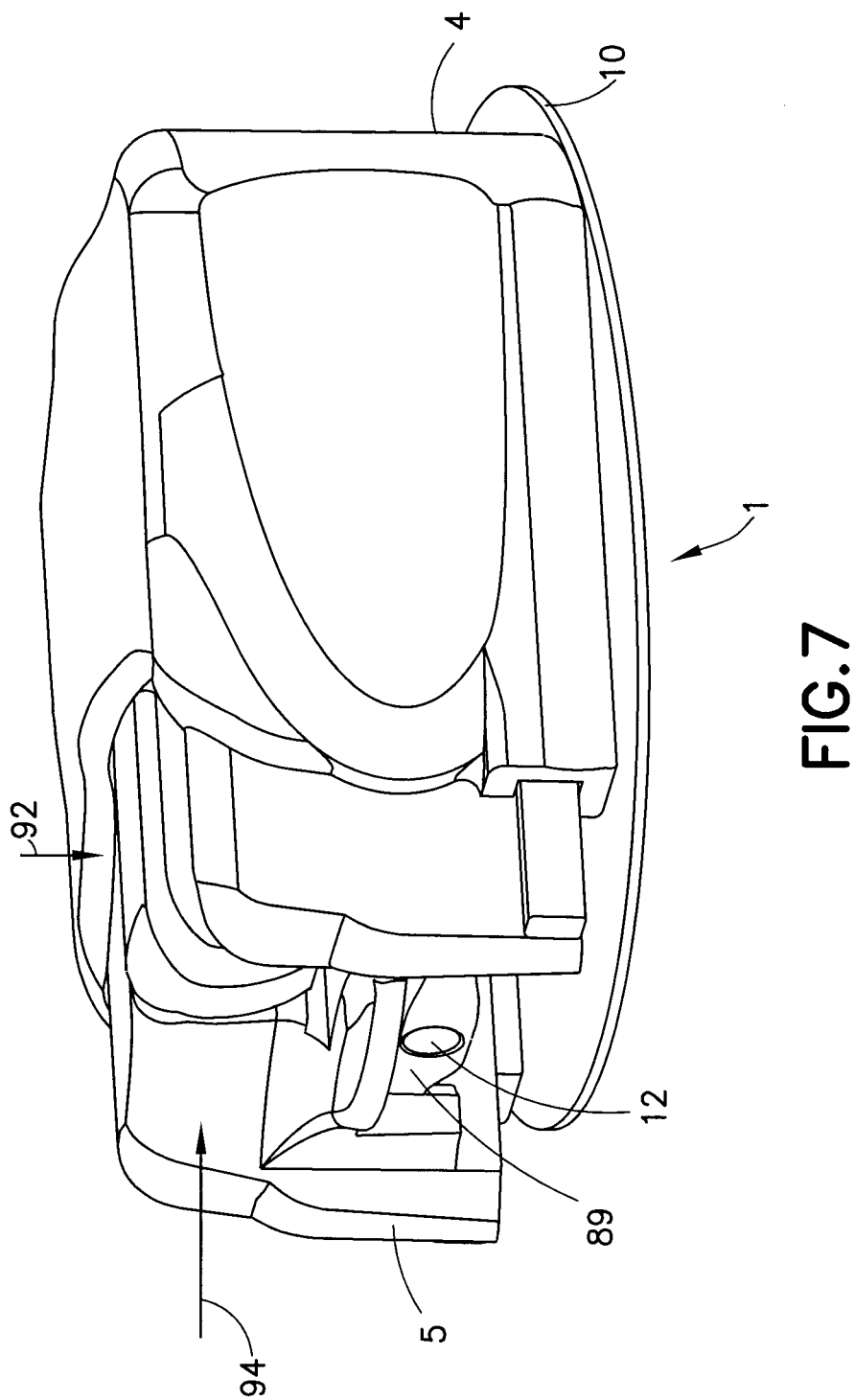
FIG. 7 is a perspective view of the infusion set and inserter during activation.

The infusion set 3 is activated by moving the flexible member 72 and squeezing the inserter 2 together, as shown in FIGS. 6 and 7. Pressing the flexible member 72 inwardly, in a direction indicated by arrow 92, causes the flexible member 72 to rotate about the living hinge 73, thereby unlocking the inserter 2. The flexible member 72 engages and moves the flexible beam 64 of the fixed inserter member 4 downwardly (indicated by arrow 93 in FIG. 6), thereby allowing the flexible member 72 of the movable inserter member 5 to slide into the fixed inserter member 4 (indicated by arrow 94 in FIG. 7).

Figure 8:
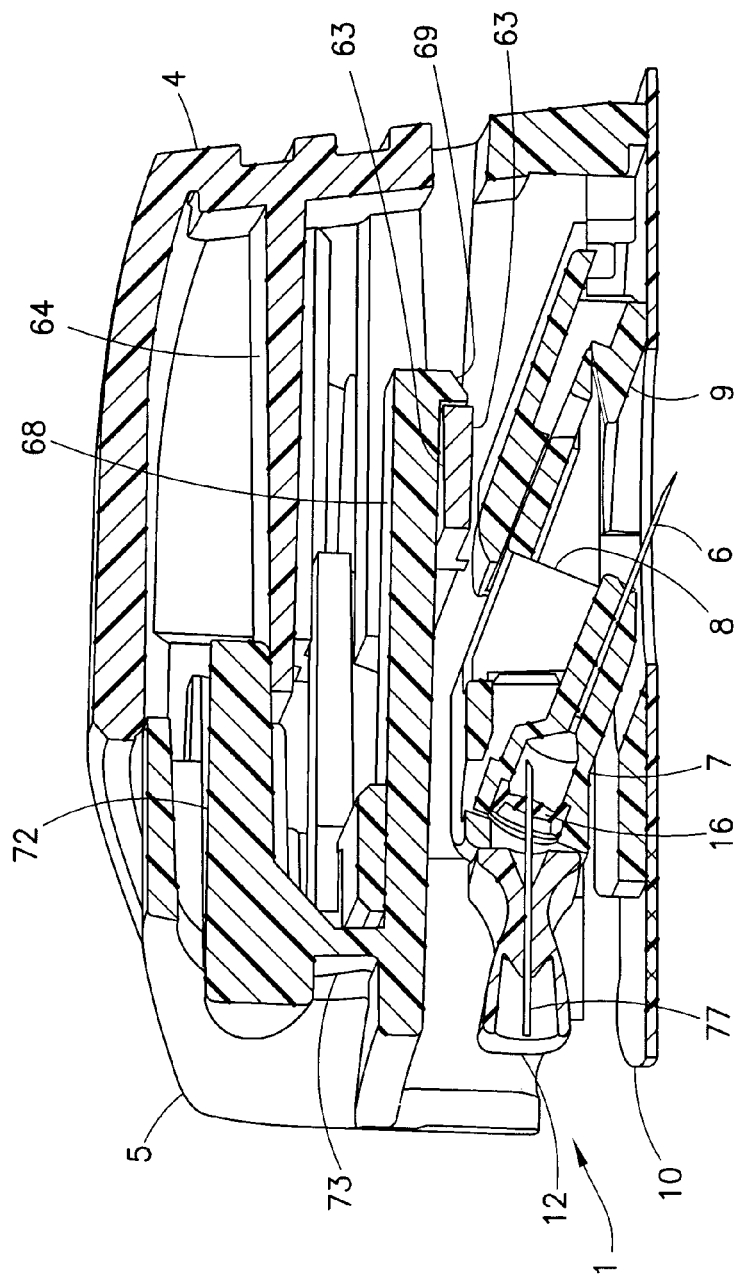
FIG. 8 is a perspective view in cross-section view of the infusion set and inserter of FIG. 1 during activation.
Figure 9:
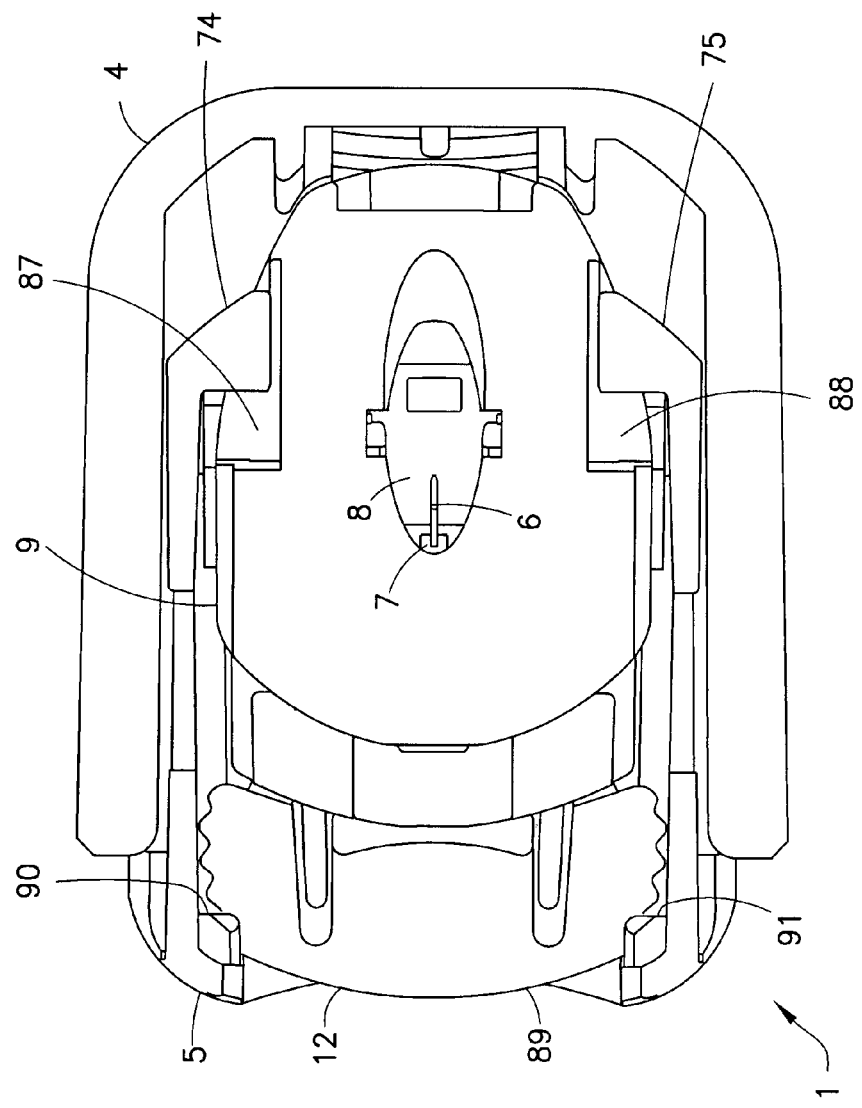
FIG. 9 is a bottom plan view of the infusion set and inserter of FIG. 1 during activation.

When the movable inserter member 5 slides into the fixed inserter member 4, as shown in FIG. 8, the movable inserter member 5 pushes the rear surface of the connector 12. As shown in FIG. 9, the inwardly extending retaining ribs 90 and 91 of the movable inserter member 5 engage and push the connector 12 in a forward direction. The connector 12 is connected to the infusion set slide member 8, such that the slide member 8 moves forwardly with forward movement of the connector 12. The slide member 8 moves into the infusion set base member 9, thereby inserting the needle 6 into the dermis layer. As shown in FIG. 8, the movable inserter member 5 is partially inserted in the fixed inserter member 4 such that the needle 6 is partially inserted. The locking feet 74 and 75 of the movable inserter member 5 still engage the longitudinally extending base member 87 and 88 of the fixed inserter member 9, as shown in FIG. 9, such that the inserter 2 cannot yet be removed from the infusion set 3. Accordingly, the inserter 2 is prevented from being removed from the infusion set 3 until the needle 6 is fully inserted, thereby preventing the user from inadvertently inserting the needle 6 only partially.

Additionally, the legs 84 and 85 of the connector tab 82, as shown in FIGS. 17 and 48-52, engage a rear end 24 of the slide member 8, thereby further facilitate forward movement of the slide member 8 with forward movement of the movable inserter member 5 to which the connector tab 82 is connected.

As shown in FIGS. 8 and 9, the forward movement of the movable inserter member 5 causes the connector 12 to move forwardly, which causes the movement of the infusion set slide member 8 toward the fully inserted second position. The outer rails 32 and 33 (FIGS. 18-23) are guided by the outer channels 46 and 47 (FIGS. 41, 42 and 44) in the infusion set fixed member 9. The outer channels 46 and 47 guide the slide member 8 forwardly at an angle α (FIGS. 6 and 44) relative to the skin surface. Preferably, the angle α is between approximately ten (10) and forty-five (45)

degrees, inclusive. More preferably, the angle α is approximately twenty (20) degrees. The needle 6 is preferably aligned with the angular insertion direction of the slide member 8 such that the needle is inserted in the substantially axial direction of the hub 7. Alternatively, the needle 6 can be offset from the insertion angle α such that the insertion direction of the needle 6 includes both axial and radial components with respect to the hub 7. In such a configuration, the orientation angle of the needle 6 is offset from the insertion slide angle of the slide member 8 and the hub 7.

Figure 11:
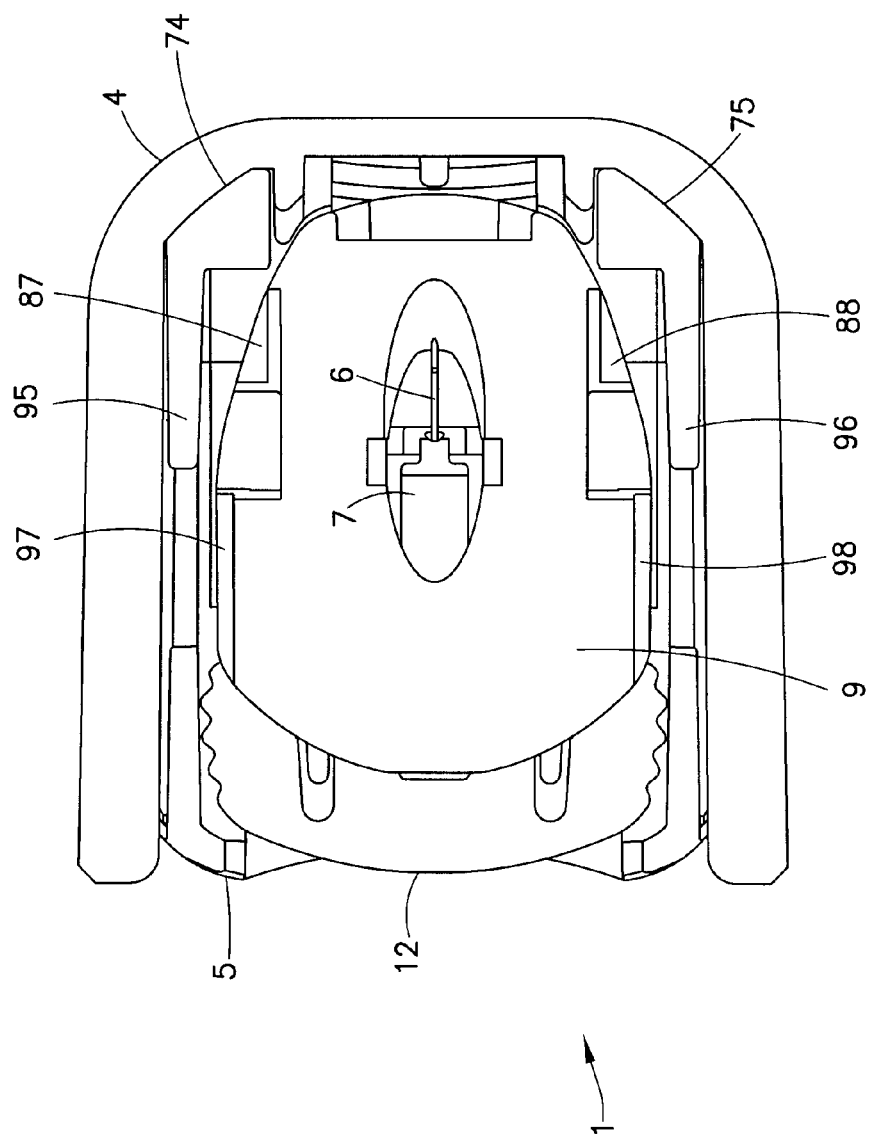
FIG. 11 is a bottom plan view of the infusion set and inserter of FIG. 10 after insertion of the cannula.
Figure 12:
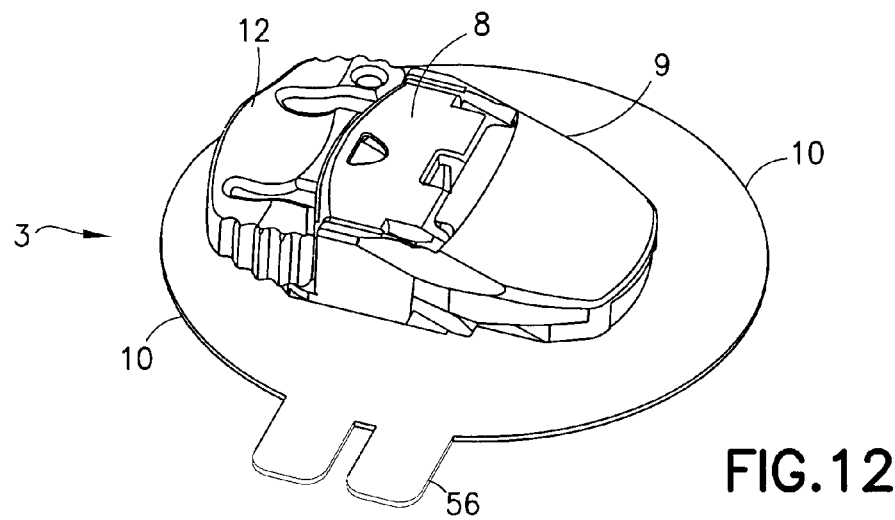
FIG. 12 is a perspective view of the infusion set of FIG. 10 after removal of the inserter.
Figure 13:
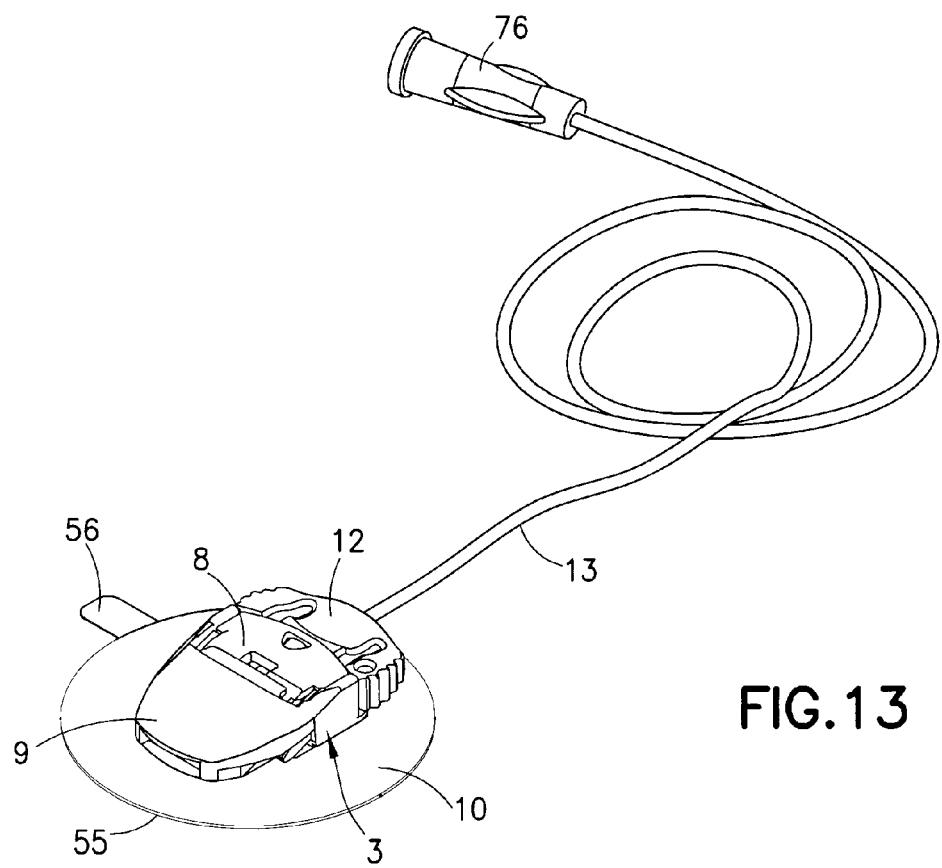
FIG. 13 is a perspective view of an infusion set prior to exposure of the adhesive pad.

Forward movement of the infusion set slide member 8 is stopped when the stop arms 38 and 39 abut the ends of inner channels 53 and 54 of the infusion set base member 9. The forward movement of the connector 12 and the movable inserter member 5 is also stopped by stopping the forward movement of the slide member 8. The infusion set 3 is now fully activated and the needle 6 is fully inserted at the angle α in the infusion site, as shown in FIGS. 10-12. The slide member 8 and the movable inserter member 5 are now in the second position. The opening 27 in the slide member 8 receives the lower tab 50 of the base member 9 when the slide member 8 moves into the second position, as shown in FIG. 10, thereby locking the slide member 8 to the base member 9 to prevent accidental removal of the inserted needle 6. Additionally, the hooks 36 and 37 of the snap arms 34 and 35 of the slide member 8 engage the upper tabs 51 and 52 extending downwardly from the upper surface 44 of the base member 9 to further secure the slide member 8 to the base member 9.

Now that the movable inserter member 5 has reached the second position, as shown in FIG. 11, the locking feet 74 and 75 of the movable inserter member 4 have moved past the longitudinally extending base members 87 and 88. Additionally, rear portions 95 and 96 of the locking feet 74 and 75 can engage rear portions 97 and 98 of the longitudinally extending base members 87 and 88 to further facilitate preventing removal of the inserter 2 until the needle 6 is fully inserted. The rear portions 95 and 96 of the locking feet 74 and 75 are clear of rear portions 97 and 98 of the longitudinally extending base members 87 and 88 when the locking feet 74 and 75 are clear of the longitudinally extending base members 87 and 88. Accordingly, inserter 2 can now be removed from the infusion set 3 by lifting the inserter upwardly with respect to the infusion set 3 and be properly disposed of. The connector 12 can be removed and connected to the slide member 8 as desired. The slide member 8 is permanently locked to the base member 9, as described above, thereby maintaining the needle 6 in its intradermally injected position until the set 3 is removed by the user.

The angular insertion of the needle 6 provides a solid anchor that maintains the infusion site. Typically, it is very difficult to maintain the position of short (i.e., 1-3 mm) needles within the skin. However, by angularly inserting the needle 6, the skin itself provides a vertical retention force. Accordingly, the inserted needle 6 is secured both vertically and horizontally. Furthermore, the angled insertion allows for more flexibility of needle or cannula choice for infusion by reducing the vertical height of the cannula opening. Also, because the needle 6 is inserted at an angle, a longer needle and/or needle opening can be used than those provided for a non-angled insertion to target the same intradermal depth.

By first adhering the infusion set assembly 1 to the skin surface, a precise mechanical foundation is provided which ensures that the needle angle, skin tensioning, stretching and/or flattening, and insertion depth are consistent. Further, in doing so, tenting is also reduced or eliminated. Still further, by isolating the needle site from the pump connection, vibrations and movements are reduced. In addition, a low-profile is provided which further isolates the needle 6 from any external forces.

By infusing into the intradermal layer of the skin, the exemplary embodiments of the present invention offer the potential for better absorption of insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

Proper alignment is accomplished by providing a solid, fixed foundation for the user to slide the movable inserter member 5 to angularly insert the needle 6. Such a solid, fixed foundation is provided by the adhesive layer 10. The skin adhesive layer secures the infusion set 3 at a desired orientation, such that the needle hub 7 and needle 6 are at a desired orientation of use, and the user is substantially prevented from holding the infusion set 3 at various angles to the insertion site. Accordingly, precise, repeatable insertions are accomplished.

Furthermore, the angle of the needle hub can be changed in this or other exemplary embodiments of the present invention to affect the insertion angle and final placement of the needle. As shown in FIG. 6, the needle 6 is aligned with the direction of travel of the hub 7. Alternatively, the needle 6 can be offset from the direction of travel of the hub 7.

Still further, in accordance with another exemplary embodiment of the present invention, the infusion set 3 can be activated without the inserter 2. The insertion is fully integrated into the infusion set 3 such that the user does not have to carry the inserter or load the infusion set into the inserter. The integrated system allows the user more freedom from carrying the inserter 2. Such a system and method is economical, simple, and compact, and provides a system of insertion that is integrated with the device. Therefore, a user can correctly insert the device without inserter 2.

Although the previously-described embodiments relate to intradermal infusion sets, the principles of the present invention are also applicable to other types of infusion sets, for example, subcutaneous infusion sets in which the patient cannula consists of a soft plastic catheter that is inserted with the aid of a rigid metal introducer needle.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion set adapted to be secured to a skin surface, comprising:
   a fixed base member connectable to the skin surface;
   a movable slide member having a needle or cannula connected thereto, movable relative to said fixed base member, said movable slide member being movable from a first position in which said needle or cannula is not exposed externally of said fixed base member to a second position in which said needle or cannula is exposed externally of said fixed base member, said movable slide member being locked to said fixed base member in said second position; and an inserter removably attachable to said infusion set, said inserter including a movable inserter member and a fixed inserter member, wherein when said inserter moves said movable slide member from said first position to said second position, said movable inserter member moves to engage said fixed base member and prevent premature withdrawal of said movable inserter member from said fixed base member, the movement of said inserter being in a direction different from the movement of said needle or cannula between said first and second positions.

2. The infusion according to claim 1, wherein said movable slide member moves in a direction not parallel to the skin surface.

3. The infusion set according to claim 1, wherein said needle or cannula is aligned with said moving direction of said movable slide member.

4. The infusion set according to claim 1, wherein said needle or cannula is offset from said moving direction of said movable slide member.

5. The infusion set according to claim 1, wherein said needle or cannula is disposed at an angle of approximately 20 degrees relative to the skin surface.

6. The infusion set according to claim 1, wherein said needle or cannula is disposed at an angle between approximately 10 and 45 degrees, inclusive, relative to the skin surface.

7. An infusion set assembly adapted to be secured to a skin surface, comprising:
   an infusion set including a fixed base member connectable to the skin surface; and
   a movable slide member having a needle or cannula connected thereto, movable relative to said fixed base member, said movable slide member being movable from a first position in which said needle or cannula is not exposed externally of said fixed base member to a second position in which said needle or cannula is exposed externally of said fixed base member; and
   an inserter removably connected to said infusion set, said inserter including a movable inserter member and a fixed inserter member, wherein
   when said inserter moves said movable slide member from said first position to said second position, said movable inserter member moves to engage said fixed base member and prevent premature withdrawal of said movable inserter member from said fixed base member; and
   said inserter actuates movement of said movable slide member by moving in a direction that is different from the movement of said needle or cannula between said first and second positions.

8. The infusion set according to claim 7, wherein said inserter is prevented from being removed from said infusion set until said movable slide member is in said second position.

9. The infusion set assembly according to claim 7, wherein said movable inserter member is movable from a first position to a second position that moves said movable slide member from said first position to said second position, said movable inserter member being substantially prevented from accidentally moving from said first position to said second position.

10. The infusion set assembly according to claim 9, wherein a flexible beam of said fixed inserter member engages a rib of said movable inserter member to prevent said movable inserter member from moving from said first position to said second position.

11. The infusion set assembly according to claim 10, wherein a flexible member of said movable inserter member is moved to deflect said flexible beam of said fixed inserter member, thereby disengaging said flexible beam from said rib of said fixed inserter member and allowing said movable inserter member to move from said first position to said second position.

12. The infusion set assembly according to claim 11, wherein said needle or cannula is disposed at an angle of approximately 20 degrees relative to the skin surface.

13. The infusion set assembly according to claim 11, wherein said needle or cannula is disposed at an angle between approximately 10 and 45 degrees, inclusive, relative to the skin surface.

14. The infusion set assembly according to claim 7, wherein a latch arm of said movable inserter member engages said fixed inserter member to prevent separation of said movable inserter member from said fixed inserter member.

15. The infusion set assembly according to claim 7, wherein said movable slide member moves from said first position to said second position in a first direction, and said movable inserter member moves from said first position to said second position in a second direction different from said first direction.

16. A method of inserting a needle or cannula of an infusion set, comprising:
   placing an infusion set having a needle or cannula on an infusion site;
   moving an inserter connected to the infusion set in a first direction to move a slide member of the infusion set from a first position to a second position in which the needle or cannula is inserted in the infusion site at a non-perpendicular angle and in which the needle or cannula is moved in a second direction different from the first direction, said slide member connected to said infusion set throughout operation; and
   engaging said inserter to a fixed base member of said infusion set to prevent premature withdrawal of said inserter from said infusion set when said inserter moves from said first position to said second position.

17. The method according to claim 16, further comprising removing the inserter from the infusion set after the needle or cannula is inserted in the infusion site.

18. The method according to claim 17, further comprising preventing removal of the inserter from the infusion set prior to insertion of the needle or cannula.

19. The method according to claim 16, further comprising manually deflecting a flexible beam on the inserter to allow movement thereof.

* * * * *